(12) United States Patent
Banerji

(10) Patent No.: US 11,517,573 B2
(45) Date of Patent: Dec. 6, 2022

(54) THERAPEUTIC COMPOSITIONS, COMBINATIONS, AND METHODS OF USE

(71) Applicant: The Institute of Cancer Research: Royal Cancer Hospital, London (GB)

(72) Inventor: Udai Banerji, London (GB)

(73) Assignee: The Institute of Cancer Research: Royal Cancer Hospital, London (GB)

( * ) Notice: Subject to any disclaimer, the term of this patent is extended or adjusted under 35 U.S.C. 154(b) by 0 days.

(21) Appl. No.: 17/470,471

(22) Filed: Sep. 9, 2021

(65) Prior Publication Data

US 2022/0031698 A1 Feb. 3, 2022

Related U.S. Application Data

(63) Continuation of application No. PCT/EP2020/075455, filed on Sep. 11, 2020.

(30) Foreign Application Priority Data

Sep. 13, 2019 (WO) .................. PCT/EP2019/074565

(51) Int. Cl.
*A61K 31/506* (2006.01)
*A61P 35/04* (2006.01)

(52) U.S. Cl.
CPC ............ *A61K 31/506* (2013.01); *A61P 35/04* (2018.01)

(58) Field of Classification Search
None
See application file for complete search history.

(56) References Cited

U.S. PATENT DOCUMENTS

| | | |
|---|---|---|
| 7,897,792 B2 | 3/2011 | Iikura et al. |
| 7,928,109 B2 | 4/2011 | Luzzio et al. |
| 8,247,411 B2 | 8/2012 | Luzzio et al. |
| 8,278,465 B2 | 10/2012 | Iikura et al. |
| 8,440,822 B2 | 5/2013 | Luzzio et al. |
| 9,133,174 B2 | 9/2015 | Murakata et al. |
| 9,962,385 B2 | 5/2018 | Pachter et al. |
| 10,406,158 B2 | 9/2019 | Pachter et al. |
| 10,450,297 B2 | 10/2019 | Luzzio et al. |
| 10,532,056 B2 | 1/2020 | Pachter et al. |
| 2011/0086837 A1 | 4/2011 | Belvin et al. |
| 2011/0092700 A1 | 4/2011 | Iikura et al. |
| 2013/0005964 A1 | 1/2013 | Luzzio et al. |
| 2014/0024653 A1 | 1/2014 | Debussche et al. |
| 2015/0190346 A1 | 7/2015 | Padval et al. |
| 2020/0038331 A1 | 2/2020 | Padval et al. |
| 2020/0147080 A1 | 5/2020 | Pachter et al. |
| 2020/0330471 A1 | 10/2020 | Pachter et al. |
| 2021/0330670 A1 | 10/2021 | Banerji |

FOREIGN PATENT DOCUMENTS

| | | | |
|---|---|---|---|
| EP | 1982982 A1 | 10/2008 | |
| EP | 2172198 A1 | 4/2010 | |
| WO | 2001017984 A1 | 3/2001 | |
| WO | 2007/091736 A1 | 8/2007 | |
| WO | 2009/014100 A1 | 1/2009 | |
| WO | 2012/045194 A1 | 4/2012 | |
| WO | 2012/095505 A1 | 7/2012 | |
| WO | 2013/170066 A1 | 11/2013 | |
| WO | 2013/182668 A1 | 12/2013 | |
| WO | 2014/059095 A1 | 4/2014 | |
| WO | 2017/004192 A1 | 1/2017 | |
| WO | WO-2019051084 A1 * | 3/2019 | ........... A61K 31/282 |
| WO | 2019/096397 A1 | 5/2019 | |
| WO | 2019/096449 A1 | 5/2019 | |

OTHER PUBLICATIONS

Stewart et al. Cancer Res. 75(14) pp. 2897-2906. (Year: 2015).*
Understanding Chemotherapy [online]. Cancer.Net Oct. 10, 2017 [retrieved on Feb. 25, 2022]. Retrieved from the internet: <http://www.cancer.net/navigating-cancer-care/how-cancer-treated/chemotherapy/understanding-chemotherapy> (Year: 2017).*
Llaurado Fernandez et al. Am J Cancer Res 6(1) pp. 2235-2251. (Year: 2016).*
Wada et al., "The dual RAF/MEK inhibitor CH5126766/RO5126766 may be a potential therapy for RAS-mutated tumor cells." PLOS ONE, 2014, 9(11): e113217.
Weaver, D. T. "Abstract A31: Merlin loss as a biomarker for defactinib (VS-6063) sensitivity: High frequency in malignant mesothelioma tumors." Molecular Cancer Therapeutics, Nov. 2013, vol. 12, No. 11 Suppl., Abstract No. A31,doi:10.1158/1535-7163. TARG-13-A31.
Xu, "Focal adhesion kinase (FAK) inhibitors VS-6063 and VS-4718 target cancer stem cells." Journal of Clinical Oncology, May 2013, vol. 31, No. 15 Suppl., Abstract No. e13523. doi:10.1200/jco.2013. 31.15_suppl.e13523.
Akinleye et al., "MEK and the inhibitors: from bench to bedside," Journal of Hematology & Oncology, 2013, 6(27): 1-11.
Aoki et al., "Optimizing the physicochemical properties of Raf/MEK inhibitors by nitrogen scanning," American Chemical Society Medicinal Chemistry Letters, 2014, 5: 309-314.
Barkan D. et al. "Beta1-Integrin: A potential therapeutic target in the battle against cancer recurrence." Clinical Cancer Research, 2011, vol. 17, No. 23, pp. 7219-7223.
Bhatt et al., "In silico docking studies of lupeol with MAPK pathway proteins-raf-1, MEK & ERK," Journal of Experimental Therapeutics and Oncology, 2017, 12: 137-140.
Chenard-Poirier et al., "Meeting library results from the biomarker-driven basket trial of RO5126766 (CH5127566), a potent RAF/MEK inhibitor, in RAS- or RAF-mutated malignancies including multiple myeloma," 2017, https://meetinglibrary.asco.org/record/144582/absract.
Cole Jr. et al. "Suppression of Pro-metastasis phenotypes expression in malignant pleural mesothelioma by the PI3K inhibitor LY294002 or the MEK inhibitor UO126." Anticancer Research, 2006, vol. 26, No. 2A, pp. 809-821.

(Continued)

*Primary Examiner* — Katherine Peebles
(74) *Attorney, Agent, or Firm* — Goodwin Procter LLP

(57) ABSTRACT

This invention relates to methods comprising administering a FAK inhibitor (e.g., VS-6063) in combination with a dual RAF/MEK inhibitor (e.g., CHS 126766) that are useful in the treatment of abnormal cell growth, such as cancer, in a subject such as humans.

12 Claims, No Drawings

(56) References Cited

OTHER PUBLICATIONS

El Touny, L. H. et al. "Combined SFK/MEK inhibition prevents metastatic outgrowth of dormant tumor cells" Journal of Clinical Investigation, Jan. 2014, vol. 124, No. 1, pp. 156-168.
El-Khoueiry A. "Abstract B75: A first in-human phase I study to evaluate the MEK1/2 inhibitor GDC-0623 in patients with advanced solid tumors." Molecular Cancer Therapeutics, Nov. 2013, vol. 12, No. 11 Suppl., Abstract No. B75, doi:10.1158/1535-7163.TARG-13-B75.
English translation of the Official Action dated Nov. 5, 2018 for Japanese patent application No. 2016-550218.
European Search Report for EP15746033 dated Aug. 18, 2017.
Gerber et al., "Phase II study of defactinib in patients with KRAS mt NSCLC—phase II study of defactinib, VS-6063, a focal adhesion kinase (FAK) inhibitor, in patients with KRAS mutant non-small lung cancer (NSCLC)," 2015, 16th World Conference on Lung Cancer, International Association for the Study of Lung Cancer.
Harris et al., "Updated efficacy and safety results from the phase I study of intermittent dosing of the dual MEK/RAF inhibitor, R05126766 in patients (pts) with RAS/RAF mutated advanced solid tumours," Journal of Clinical Oncology, 2016, 34(15_suppl): 2582.
Heist R. S. "Combination of a MEK inhibitor, pimasertib (MSC1936369B), and a PI3K/mTOR inhibitor, SAR 245409, in patients with advanced solid tumors: Results of a phase Ib dose-escalation trial." Journal of Clinical Oncology, 2013, vol. 31, No. 15, Suppl., Abstract No. 2530.
History of Changes for Study NCT00773526, "An open label dose-escalation study to evaluate safety, pharmacokinetics and anti-tumor activity of R05126766, a dual raf and MEK inhibitor, administered orally as monotherapy in patients with advanced tumors," dated Nov. 2, 2016.
History of Changes for Study NCT02407509, "A phase I trial of R05126766 (a dual RAF/MEK inhibitor) exploring intermittent, oral dosing regimens in patients with solid tumours or multiple myeloma, with an expanson to explore intermittent dosing in combination with everolimus," dated Nov. 1, 2018.
History of Changes for Study NCT03875820, "FRAME: A phase I trial of the combination of VS-6063 (FAK inhibitor) and R05126766 (CH5126776) (a dual RAF/MEK inhibitor) in patients with advanced solid tumours," dated Apr. 9, 2020.
History of Changes for Study NCT03875820, "FRAME: A phase I trial of the combination of VS-6063 (FAK inhibitor) and R05126766 (CH5126776) (a dual RAF/MEK inhibitor) in patients with advanced solid tumours," dated Feb. 28, 2020.
History of Changes for Study NCT03875820, "FRAME: A phase I trial of the combination of VS-6063 (FAK inhibitor) and R05126766 (CH5126776) (a dual RAF/MEK inhibitor) in patients with advanced solid tumours," dated Jun. 25, 2020.
History of Changes for Study NCT03875820, "FRAME: A phase I trial of the combination of VS-6063 (FAK inhibitor) and R05126766 (CH5126776) (a dual RAF/MEK inhibitor) in patients with advanced solid tumours," dated Mar. 15, 2019.
History of Changes for Study NCT03875820, "FRAME: A phase I trial of the combination of VS-6063 (FAK inhibitor) and R05126766 (CH5126776) (a dual RAF/MEK inhibitor) in patients with advanced solid tumours," dated Nov. 21, 2019.
History of Changes for Study NCT03875820, "FRAME: A phase I trial of the combination of VS-6063 (FAK inhibitor) and R05126766 (CH5126776) (a dual RAF/MEK inhibitor) in patients with advanced solid tumours," dated Sep. 11, 2020.
Honda et al., "Phase I and pharmacokinetic/pharmacodynamic study of R05126766, a first-in-class dual Raf/MEK inhibitor, in Japanese patients with advanced solid tumors," Cancer Chemotherapy Pharmacology, 2013, 72: 577-584.
International Search Report and Written Opinion for International Application No. PCT/EP2017/079506, dated Aug. 13, 2018.
International Search Report and Written Opinion for International Application No. PCT/EP2018/062805, dated Aug. 16, 2018.
International Search Report and Written Opinion for International Application No. PCT/EP2019/074565, dated Jun. 2, 2020.
International Search Report and Written Opinion for International Application No. PCT/EP2020/056642, dated Jun. 24, 2020.
International Search Report and Written Opinion for International Application No. PCT/EP2020/075455, dated Nov. 24, 2020.
International Search Report for PCT/US2015/14843 dated Apr. 21, 2015.
Ishii et al., "Enhanced inhibiion of ERK signaling by a novel allosteric MEK inhibitor, CH5126766, that suppresses feedback reactivation of RAF activity," Cancer Res. 2013, 73(13): 4050-4060.
Jones et al., "A phase I study of VS-6063, a second-generation focal adhesion kinase inhibitor, in patients with advanced solid tumors," Investigational New Drugs, 2015, 33(5): 1100-1107.
Kolev, V. N. "Abstract A39: FAK inhibitors VS-6063 and VS-4718 preferentially target ovarian cancer stem cells." Clinical Cancer Research, Oct. 2013, vol. 19, No. 19 Suppl., Abstract No. A39.
Kraeber-Bodéré et al., "Differences in the biologic activity of 2 novel MEK inhibitors revealed by F-FDG PET: Analysis of imaging data from 2 phase I trials," The Journal of Nuclear Medicine, 2012, 53(12): 1836-1846.
Lito et al., "Disruption of CRAF-mediated MEK activation is required for effective MEK inhibition in KRAS mutant tumors," Cancer Cell. 2014, 25(5): 697-710.
Martinez-Garcia et al., "First-in-human, phase I dose-escalation study of the safety, pharmacokinetics, and pharmacodynamics of R05126766, a first-in-class dual MEK/RAF inhibitor in patients with solid tumors," Clinical Cancer Research, 2012, 18(17):4806-4819.
Matsumoto, S. "Combination efficacy of mTOR and MEK inhibitor in malignant pleural mesothelioma (MPM)." Journal of Clinical Oncology, 2013, vol. 31, No. 15 Suppl., Abstract No. e18557, doi:10.1200/jco.2013.31.15_suppl.e18557.
Milella et al. "Beyond single pathway inhibition: MEK inhibitors as a a platform for the development of pharmacological combindations with synergistic anti-leukemic effects," Current Pharmaceutical Design, 2005, 11, 2779-2795.
Miller et al., "MEK1/2 inhibitors in the treatment of gynecologic malignancies," Gynecologic Oncology, 2014, 133: 128-137.
Miyoshi et al. "Antitumor activity of MEK and PI3K inhibitors against malignant pleural mesothelioma cells in vitro and in vivo." International Journal of Oncology, 2012, vol. 41, No. 2, pp. 449-456.
Pachter, J. A. "Sensitivity of malignant mesothelioma lacking merlin to the FAK inhibitor VS-6063: Evaluation of merlin/NF2 status in clinical samples." Journal of Clinical Oncology, Nov. 2013, vol. 31, No. 15 Suppl., Abstract No. e18541, doi:10.1200/jco.2013.31.15_suppl.e18541.
Patel, M. R. "Abstract A69: Phase 1/1b study of the FAK inhibitor defactinib (VS-6063) in combination with weekly paclitaxel for advanced ovarian cancer." Molecular Cancer Therapeutics, Nov. 2013, vol. 12, No. 11 Suppl., Abstract No. A69, doi:10.1158/1535-7163.TARG-13-A69.
Ring, J. E. "Abstract B283: Defactinib (VS-6063) targets cancer stem cells directly and through inhibition of tumor-associated macrophages and cytokine production." Molecular Cancer Therapeutics, Nov. 2013, vol. 12, No. 11 Suppl., Abstract No. B283, doi:10.1158/1535-7163.TARG-13-B283.
Shapiro, I. M. "Abstract C262: Malignant mesothelioma lacking merlin shows enhanced sensitivity to the FAK inhibitor defactinib (VS-6063): Elucidation of the merlin-FAK relationship." Molecular Cancer Therapeutics, Nov. 2013, vol. 12, No. 11 Suppl., Abstract No. C262, doi:10.1158/1535-7163.TARG-13-C262.
Shimzu et al., "A first-in-Asian phase 1 study to evaluate safety, pharmacokinetics and clinical activity of VS-6063, a focal adhesion kinase (FAK) inhibitor in Japanese patients with advanced solid tumors," Cancer Chemotherapy and Pharmacology, 2016, 77(5): 997-1003.
Sulzmaier et al., "FAK in cancer: mechanistic findings and clinical applications," Nature reviews, Cancer, 2014, 14(9): 598-610.

(56) References Cited

OTHER PUBLICATIONS

Tanaka et al., "MEK inhibitors as a novel therapy for neuroblastoma: Their in vitro effects and predicting their efficacy," Journal of Pediatric Surgery, 2016, 51: 2074-2079.
Tegnebratt et al., "[18F]FDG-PET imaging is an early non-invasive pharmacodynamic biomarker for a first-in-class dual MEK/Raf inhibitor, RO5126766 (CH5126766), in preclinical xenograft models," EJNMMI Research, 2013, 3(67): 1-11.
Ueyama et al., "Inhibition of MEK1 signaling pathway in the liver ameliorates insulin resistance," Journal of Diabetes Research, 2016, 1-13.
Van Dort et al., "Dual inhibition of allosteric mitogen-activated protein kinase (MEK) and phosphatidylinositol 3-kinase (PI3K) oncogenic targets with a bifunctional inhibitor," Bioorg Med Chem., 2015, 23(7): 1386-1394.
Vidal, Abstract C271: FAK inhibitor defactinib (VS-6063) enhances the efficacy of paclitaxel and preferentially targets ovarian cancer stem cells. Molecular Cancer Therapeutics, Nov. 2013, vol. 12, No. 11 Suppl., Abstract No. C271, doi:10.1158/1535-7163.TARG-13-C271.
Vu et al. "Green tea epigallocatechin gallate exhibits anticancer effect in human pancreatic carcinoma cells via the inhibition of both focal adhesion kinase and insulin-like growth factor-I receptor." Journal of Biomedicine and Biotechnology, 2010, 1-8.
Chenard-Poirier et al., "Results from the biomarker-driven basket trial of RO5126766 (CH5126766), a potent RAF/MEK inhibitor, in RAS- or RAF-mutated malignancies, including multiple myeloma" (2017) ASCO annual meeting, presentation slides, 9 pages.
History of Changes for Study NCT02407509, "Phase I trial of RO5126766 (DDU RAF/MEK)," dated Apr. 3, 2015.
History of Changes for Study NCT03681483, "RO5126766 for patients with advanced KRAS-mutant lung cancer," dated Nov. 2, 2018.
History of Changes for Study NCT04625270, "A study of VS-6766 v. VS-6766 + defactinib in recurrent low-grade serous ovarian cancer with and without a KRAS mutation," dated Nov. 12, 2020.
History of Changes for Study NCT04620330, "A study of VS-6766 v. VS-6766 + defactinib in recurrent G12V or other KRAS-mutant non-small cell lung cancer," dated Nov. 6, 2020.
Monk et al., "MILO/ENGOT-ov11: Binimetinib Versus Physician's Choice Chemotherapy in Recurrent or Persistent Low-Grade Serous Carcinomas of the Ovary, Fallopian Tube, or Primary Peritoneum", Journal of Clinical Oncology, 38(32): 3753-3770, Aug. 21, 2020.
Shapiro et al., "Phase Ib study of the MEK inhibitor cobimetinib (GDC-0973) in combination with the PI3K inhibitor pictilisib (GDC-0941) in patients with advanced solid tumors", Invest. New Drugs (2020) 38:419-432.
Gershenson et al., "Trametinib versus standard of care in patients with recurrent low-grade serous ovarian cancer (GOG 281/LOGS):an international, randomised, open-label, multicentre, phase 2/3 trial", www.thelancet.com, vol. 399: 541-553, Feb. 5, 2022.
Mak et al., "A phase Ib dose-finding, pharmacokinetic study of the focal adhesion kinase inhibitor GSK2256098 and trametinib in patients with advanced solid tumours", British Journal of Cancer (2019) 120:975-981.
Shapiro et al., "A phase Ib open-label dose escalation study of the safety, pharmacokinetics, and pharmacodynamics of cobimetinib (GDC-0973) and ipatasertib (GDC-0068) in patients with locally advanced or metastatic solid tumors", Invest. New Drugs (Feb. 2021) 39(1):163-174.
Weekes et al., "A Phase Ib Study to Evaluate the MEK Inhibitor Cobimetinib in Combination with the ERK1/2 Inhibitor GDC-0994 in Patients with Advanced Solid Tumors", The Oncologist (2020); 25:833-e1438.
Aung et al., "A phase II trial of GSK2256098 and trametinib in patients with advanced pancreatic ductal adenocarcinoma (PDAC)(MOBILITY-002 Trial, NCT02428270)", Journal of Clinical Oncology, 36, No. 4 suppl. (Feb. 1, 2018), 409-409.
Algazi et. al., "Continuous versus intermittent BRAF and MEK inhibition in patients with BRAF mutated melanoma: a randomized phase 2 trial", Nat Med. Oct. 2020; 26(10): 1564-1568.
Gonzalez-Cao et al., "Intermittent BRAF inhibition in advanced BRAF mutated melanoma results of a phase II randomized trial", Nature Communications (2021), 12:7008, 6 pages.

* cited by examiner

THERAPEUTIC COMPOSITIONS, COMBINATIONS, AND METHODS OF USE

CROSS-REFERENCE TO RELATED APPLICATIONS

This application is a continuation of International Application PCT/EP2020/075455, filed Sep. 11, 2020, which claims priority to International Application PCT/EP2019/074565, filed Sep. 13, 2019, the contents of each of which are incorporated herein by reference in their entirety.

BACKGROUND

Convincing evidence suggests that focal adhesion kinase (FAK), i.e., PTK2, a cytoplasmic, non-receptor tyrosine kinase, plays an essential role in cell-matrix signal transduction pathways (Clark and Brugge 1995, *Science* 268: 233-239) and its aberrant activation is associated with an increase in the metastatic potential of tumors (Owens et al. 1995, *Cancer Research* 55: 2752-2755). FAK was originally identified as a 125 kDa protein highly tyrosine-phosphorylated in cells transformed by v-Src. FAK is encoded by the PTK2 gene in humans. FAK was subsequently found to be a tyrosine kinase that localizes to focal adhesions, which are contact points between cultured cells and their underlying substratum and sites of intense tyrosine phosphorylation. FAK is phosphorylated and, thus, activated in response to extracellular matrix (ECM)-binding to integrins. Recently, studies have demonstrated that an increase in FAK mRNA levels accompanied invasive transformation of tumors and attenuation of the expression of FAK (through the use of antisense oligonucleotides) induces apoptosis in tumor cells (Xu et al. 1996, *Cell Growth and Diff* 7: 413-418). In addition to being expressed in most tissue types, FAK is found at elevated levels in most human cancers, for example in highly invasive metastases, including cancers of the thyroid, prostate, cervix, colon, rectum, oral epithelium, ovary, and breast. Compounds, compound combinations, compositions, and methods for inhibiting FAK in a subject are therefore desirable.

Components of the RAS/RAF/MEK/ERK signal transduction pathway also represent opportunities for the treatment of abnormal cell growth, e.g., cancer.

WO 2015/120289 discloses a method of treating a subject having cancer, the method comprising administering to the subject a therapeutically effective amount of a FAK inhibitor (e.g., VS-6063), in combination with a MEK inhibitor (e.g., GDC-0623, cobimetinib, trametinib, pimasertib, AZD6244), thereby treating the subject.

WO 2014/059095 and Br J Cancer. 2019 May; 120(10): 975-981 relate to use of a combination comprising a specific FAK inhibitor and a specific MEK inhibitor (trametinib) in the treatment of cancer.

SUMMARY

A combination of a FAK inhibitor (e.g., VS-6063) and a dual RAF/MEK inhibitor (e.g., CH5126766) may enhance the generation and effectiveness of tumor-specific cytotoxic lymphocytes and provide a promising approach for more effectively treating a disease or disorder described herein (e.g., abnormal cell growth, e.g., cancer (e.g., a cancer described herein)). VS-6063, or a pharmaceutically acceptable salt thereof (a FAK inhibitor), may be used in combination with CH5126766, or a pharmaceutically acceptable salt thereof (a dual RAF/MEK inhibitor) to treat a disease or disorder described herein, e.g., abnormal cell growth (e.g., a cancer described herein).

Therefore, provided herein is a certain combination (e.g., a combination as described herein (e.g., a FAK inhibitor in combination with a dual RAF/MEK inhibitor)), which can be used, for example, to treat abnormal cell growth, such as cancer (e.g., a cancer with a RAS mutation), in a subject (e.g., humans).

Described herein is a method of treating a subject having cancer, the method comprising administering to the subject a therapeutically effective amount of VS-6063, or a pharmaceutically acceptable salt thereof (a FAK inhibitor), in combination with CH5126766, or a pharmaceutically acceptable salt thereof (a dual RAF/MEK inhibitor), thereby treating the subject, wherein the cancer is a cancer with a RAS mutation. In some embodiments, the RAS mutation is a KRAS mutation or NRAS mutation.

Described herein is a method of treating a subject having cancer, the method comprising administering to the subject a therapeutically effective amount of VS-6063, or a pharmaceutically acceptable salt thereof, in combination with a dual RAF/MEK inhibitor, wherein the dual RAF/MEK inhibitor is CH5126766, or a pharmaceutically acceptable salt thereof. In some embodiments, the cancer is caused by a mutation in RAS, BRAF, or NF-1. In some embodiments, the cancer is a cancer with a RAS mutation. In other aspects, the cancer has a KRAS mutation or NRAS mutation.

Described herein is a use of VS-6063, or a pharmaceutically acceptable salt thereof, in combination with a dual RAF/MEK inhibitor, for treating cancer, wherein the dual RAF/MEK inhibitor is CH5126766, or a pharmaceutically acceptable salt thereof. In some embodiments, the cancer is caused by a mutation in RAS, BRAF, or NF-1. In some embodiments, the cancer has a RAS mutation. In other aspects, the cancer has a KRAS mutation or NRAS mutation.

Described herein is a method of treating a subject having cancer, the method comprising administering to the subject a therapeutically effective amount of CH5126766, or a pharmaceutically acceptable salt thereof, in combination with a FAK inhibitor, wherein the FAK inhibitor is VS-6063, or a pharmaceutically acceptable salt thereof. In some embodiments, the cancer is caused by a mutation in RAS, BRAF, or NF-1. In some embodiments, the cancer has a RAS mutation. In other aspects, the cancer has a KRAS mutation or NRAS mutation.

Described herein is a use of CH5126766, or a pharmaceutically acceptable salt thereof, in combination with a FAK inhibitor, for treating cancer, wherein the FAK inhibitor is VS-6063, or a pharmaceutically acceptable salt thereof. In some embodiments, the cancer is caused by a mutation in RAS, BRAF, or NF-1. In some embodiments, the cancer has a RAS mutation. In other aspects, the cancer has a KRAS mutation or NRAS mutation.

Described herein is a method of treating a subject having cancer, the method comprising administering to the subject a therapeutically effective amount of a dual RAF/MEK inhibitor, in combination with a FAK inhibitor, wherein the dual RAF/MEK inhibitor is CH5126766, or a pharmaceutically acceptable salt thereof, and the FAK inhibitor is VS-6063, or a pharmaceutically acceptable salt thereof.

Described herein is a use of a dual RAF/MEK inhibitor, in combination with a FAK inhibitor, for treating cancer, wherein the dual RAF/MEK inhibitor is CH5126766, or a pharmaceutically acceptable salt thereof, and the FAK inhibitor is VS-6063, or a pharmaceutically acceptable salt thereof.

In some embodiments, the cancer is caused by a mutation in RAS, BRAF, or NF-1.

In some embodiments, the cancer is selected from ovarian cancer, lung cancer, colon cancer, and pancreatic cancer. In some embodiments, the cancer is ovarian cancer. In some embodiments, the ovarian cancer is low grade serous ovarian cancer. In some embodiments, the cancer is lung cancer. In other embodiments, the cancer is colon cancer. In some embodiments, the cancer is pancreatic cancer. In some embodiments, the cancer is selected from low grade serous ovarian cancer, lung cancer, colon cancer, and pancreatic cancer.

In some aspects, the dual RAF/MEK inhibitor (e.g., CH5126766) is dosed twice a week. In some aspects, the FAK inhibitor (e.g., VS-6063) is dosed twice daily. In other aspects, the FAK inhibitor (e.g., VS-6063) is dosed once daily. In some embodiments, the dual RAF/MEK inhibitor (e.g., CH5126766) and the FAK inhibitor (e.g., VS-6063) are dosed for at least three weeks. In some embodiments, the dual RAF/MEK inhibitor (e.g., CH5126766) and the FAK inhibitor (e.g., VS-6063) are independently dosed cyclically for three weeks on and then one week off. In some embodiments, both of the dual RAF/MEK inhibitor (e.g., CH5126766) and the FAK inhibitor (e.g., VS-6063) are simultaneously dosed cyclically for three weeks on and then one week off.

In some aspects, the dual RAF/MEK inhibitor (e.g., CH5126766) is dosed at about 0.5 mg to about 10 mg. In further embodiments, the dual RAF/MEK inhibitor (e.g., CH5126766) is dosed at about 4 mg. In other embodiments, the dual RAF/MEK inhibitor (e.g., CH5126766) is dosed at 3.2 mg. In some embodiments, the FAK inhibitor (e.g., VS-6063) is dosed at about 100 mg to about 400 mg. In some embodiments, the FAK inhibitor (e.g., VS-6063) is dosed at about 100 mg to about 500 mg. In further embodiments, the FAK inhibitor (e.g., VS-6063) is dosed at about 200 mg to about 500 mg. In other embodiments, the FAK inhibitor (e.g., VS-6063) is dosed at about 200 mg to about 600 mg. In some aspects, the dual RAF/MEK inhibitor (e.g., CH5126766) is dosed at about 0.5 mg to about 10 mg and the FAK inhibitor (e.g., VS-6063) is dosed at about 100 mg to about 400 mg. In some embodiments, the dual RAF/MEK inhibitor (e.g., CH5126766) is dosed at about 4 mg twice a week and the FAK inhibitor (e.g., VS-6063) is dosed at about 200 mg twice daily. In some embodiments, the dual RAF/MEK inhibitor (e.g., CH5126766) is dosed at 3.2 mg twice a week and the FAK inhibitor (e.g., VS-6063) is dosed at 200 mg twice daily. In some embodiments, the dual RAF/MEK inhibitor (e.g., CH5126766) is dosed at about 4 mg twice a week and the FAK inhibitor (e.g., VS-6063) is dosed at about 400 mg twice daily. In some embodiments, the dual RAF/MEK inhibitor (e.g., CH5126766) is dosed at 3.2 mg twice a week and the FAK inhibitor (e.g., VS-6063) is dosed at 400 mg twice daily.

DETAILED DESCRIPTION OF THE INVENTION

Described herein, among other things, are methods for treating abnormal cell growth, e.g., cancer, the method comprising administering a FAK inhibitor and a dual RAF/MEK inhibitor, wherein the FAK inhibitor is VS-6063, or a pharmaceutically acceptable salt thereof, and the dual RAF/MEK inhibitor is CH5126766, or a pharmaceutically acceptable salt thereof.

Methods of Treatment and Administration

The methods described herein relate to treating a subject (e.g., a human subject) suffering from a disease or disorder described herein (e.g., abnormal cell growth, e.g., cancer (e.g., a cancer described herein)) with a FAK inhibitor in combination with a dual RAF/MEK inhibitor, wherein the FAK inhibitor is VS-6063, or a pharmaceutically acceptable salt thereof, and the dual RAF/MEK inhibitor is CH5126766, or a pharmaceutically acceptable salt thereof. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the method comprises administration of a FAK inhibitor (e.g., VS-6063) before administration of a dual RAF/MEK inhibitor (e.g., CH5126766). In some embodiments, the method comprises administration of a FAK inhibitor (e.g., VS-6063) after administration of a dual RAF/MEK inhibitor (e.g., CH5126766). In some embodiments, the method comprises administration of a FAK inhibitor (e.g., VS-6063) concurrently with administration of a dual RAF/MEK inhibitor (e.g., CH5126766). In some embodiments, the FAK inhibitor is VS-6063 (PF-04554878; defactinib), or a pharmaceutically acceptable salt thereof. In some embodiments, the dual RAF/MEK inhibitor is CH5126766, or a pharmaceutically acceptable salt thereof.

Tumor Microenvironment

The combination of compounds described herein is also directed to methods of modulating or conditioning the tumor microenvironment in a subject (e.g., a subject with a cancer described herein). As used herein, the "tumor microenvironment" refers to the cellular environment in which a tumor exists, including surrounding blood vessels, immune cells, fibroblasts, bone marrow-derived inflammatory cells, lymphocytes, signaling molecules and the extracellular matrix (ECM). The tumor and the surrounding microenvironment are closely related and interact constantly. Tumors can influence the microenvironment by releasing extracellular signals, promoting tumor angiogenesis and inducing peripheral immune tolerance, while the immune cells in the microenvironment can affect the growth and evolution of cancerous cells.

As used herein, the term "immunosuppressive cell" refers to a cell that contributes to or promotes an immunosuppressive tumor microenvironment. The presence of a population of immunosuppressive cells in a tumor microenvironment, also referred to herein as "tumor-associated immunosuppressive cells" increases the tumor's resistance to an immune response, resulting in tumor protection, tumor escape, and/or tumor metastasis. Unless countered in some manner, tumor-associated immunosuppressive cells can decrease the efficacy of immune-mediated anti-cancer treatments. There are large numbers of tumor-associated immunosuppressive cells, which include myeloid-derived suppressor cells (MDSCs) and regulatory T cells.

In some embodiments, the combination of compounds described herein enhances the effectiveness of tumor-specific cytotoxic lymphocytes or anti-tumor cytotoxic T cells. In some embodiments, a FAK inhibitor (e.g., VS-6063) as described herein targets immunosuppressive cells in the tumor microenvironment. In some embodiments, a FAK inhibitor (e.g., VS-6063) as described herein acts as a barrier to T cell infiltration by way of tumor-stroma modulation of dense desmoplastic stroma and/or FAK-regulated pro-inflammatory and/or pro-fibrotic cytokine secretion. In some embodiments, BRAF inhibition activates the stroma cells (e.g., cancer activated fibroblasts, cell adhesion factor) leading to FAK-dependent cancer survival signaling (e.g., in melanoma).

Abnormal Cell Growth

The methods described herein are directed to the treatment of abnormal cell growth in a subject (e.g., a human subject). Abnormal cell growth, as used herein and unless otherwise indicated, refers to cell growth that is independent of normal regulatory mechanisms (e.g., loss of contact inhibition). This includes the abnormal growth of: (1) tumor cells (tumors) that proliferate, for example, by expressing a mutated tyrosine kinase or overexpression of a receptor tyrosine kinase; (2) benign and malignant cells of other proliferative diseases, for example, in which aberrant tyrosine kinase activation occurs; (3) any tumors that proliferate, for example, by receptor tyrosine kinases; (4) any tumors that proliferate, for example, by aberrant serine/threonine kinase activation; and (5) benign and malignant cells of other proliferative diseases, for example, in which aberrant serine/threonine kinase activation occurs. Abnormal cell growth can refer to cell growth in epithelial (e.g., carcinomas, adenocarcinomas); mesenchymal (e.g., sarcomas (e.g., leiomyosarcoma, Ewing's sarcoma)); hematopoetic (e.g., lymphomas, leukemias, myelodysplasias (e.g., pre-malignant)); or other (e.g., mesothelioma, and other tumors of unknown origin) cells.

In some embodiments, the method is effective in treating non-hematologic malignancies. In some embodiments, the method is effective in treating pancreas, non small cell lung carcinoma (NSCLC), small cell lung carcinoma (SCLC), mesothelioma, breast and ovarian cancer. In an embodiment, the breast cancer is triple-negative breast cancer (e.g., breast cancer which does not express the genes for the estrogen receptor, progesterone receptor, and Her2/neu). In an embodiment, the lung cancer is non-small cell lung cancer (NSCLC), e.g., KRAS mutant NSCLC. In an embodiment, the ovarian cancer is advanced ovarian cancer (e.g., advanced ovarian cancer or metastatic ovarian cancer). In an embodiment, the ovarian cancer is low grade serous ovarian cancer. In an embodiment, the low grade serous ovarian cancer is KRAS mutant low grade serous ovarian cancer. In an embodiment, the method is effective in treating mesothelioma (e.g., malignant pleural mesothelioma, e.g., surgically resectable malignant pleural mesothelioma). In some embodiments, the cancer is pancreatic cancer.

Neoplastic Disorders

Abnormal cell growth can refer to a neoplastic disorder. A "neoplastic disorder" is a disease or disorder characterized by cells that have the capacity for autonomous growth or replication, e.g., an abnormal state or condition characterized by proliferative cell growth. An abnormal mass of tissue as a result of abnormal cell growth or division, or a "neoplasm", can be benign, pre-malignant (carcinoma in situ) or malignant (cancer).

Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Treatment with the compound may be in an amount effective to ameliorate at least one symptom of the neoplastic disorder, e.g., reduced cell proliferation, reduced tumor mass, etc.

Cancer

In some embodiments, the methods of the present invention may be useful in the treatment of cancer, including, for example, solid tumors, soft tissue tumors, and metastases thereof. In some embodiments, the methods of the present invention may be useful in the treatment of cancer in which the MEK-ERK pathway is activated. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer (e.g., Hepatocellular carcinoma), non-small cell carcinoma of the lung, pancreatic (e.g., metastatic pancreatic adenocarcinoma) and cancer of the small intestine.

The cancer can also include uterine cancer (endometrial cancer, uterine neoplasm, cervical cancer, etc.), biliary cancer, and biliary tract cancer (cholangiocarcinoma, bile duct cancer, gallbladder cancer, etc.).

The cancer can be a primary tumor, i.e., located at the anatomical site of tumor growth initiation. The cancer can also be metastatic, i.e., appearing at least a second anatomical site other than the anatomical site of tumor growth initiation. The cancer can be a recurrent cancer, i.e., cancer that returns following treatment, and after a period of time in which the cancer was undetectable. The recurrent cancer can be anatomically located locally to the original tumor, e.g., anatomically near the original tumor; regionally to the original tumor, e.g., in a lymph node located near the original tumor; or distantly to the original tumor, e.g., anatomically in a region remote from the original tumor.

The cancer can also have a RAS mutation, meaning that the cancer is caused by a mutation of a RAS gene (HRAS, NRAS, or KRAS). The cancer could also have a KRAS mutation, meaning that the cancer is caused by a mutation of the KRAS gene. The cancer could also have a NRAS mutation, meaning that the cancer is caused by a mutation of the NRAS gene. In some embodiments, the cancer is ovarian cancer caused by a mutation of a RAS gene (for example, KRAS gene). In some embodiments, the cancer is low grade ovarian cancer or mucinous ovarian cancer, both are caused by a mutation of a RAS gene (for example, KRAS gene). In some embodiments, the cancer is lung cancer caused by a mutation of a RAS gene (for example, KRAS gene). In some embodiments, the cancer is colon cancer caused by a mutation of a RAS gene (for example, KRAS gene or NRAS gene). In some embodiments, the cancer is pancreatic cancer caused by a mutation of a RAS gene (for example, KRAS gene).

The cancer can also include, for example, epithelial cancers, breast, lung, pancreatic, colorectal (e.g., metastatic colorectal, e.g., metastatic KRAS mutated), prostate, head and neck, melanoma, acute myelogenous leukemia, and glioblastoma. Exemplary breast cancers include, triple negative breast cancer, basal-like breast cancer, claudin-low breast cancer, invasive, inflammatory, metaplastic, and advanced Her-2 positive or ER-positive cancers resistant to therapy.

Examples of genes mutated in the cancer also include EGFR, FGFR, ALK, ROS1, PI3K, NF-1, BRAF, HRAS, KRAS and NRAS. The cancer is preferably a KRAS mutant and/or NRAS mutant cancer, and more preferably it is KRAS mutant or NRAS mutant colon cancer, or a KRAS mutant solid cancer (preferably ovarian cancer, lung cancer (particularly non-small-cell lung cancer), colon cancer, and pancreatic cancer).

Other cancers include brain, abdominal, esophagus, gastrointestinal, glioma, liver, tongue, neuroblastoma, osteosarcoma, ovarian, retinoblastoma, Wilm's tumor, multiple myeloma, skin, lymphoma, blood and bone marrow cancers (e.g., advanced hematological malignancies, leukemia, e.g., acute myeloid leukemia (e.g., primary or secondary), acute lymphoblastic leukemia, acute lymphocytic leukemia, T cell leukemia, hematological malignancies, advanced myeloproliferative disorders, myelodysplastic syndrome, relapsed or refractory multiple myeloma, advanced myeloproliferative disorders), retinal, bladder, cervical, kidney, endometrial, meningioma, lymphoma, skin, uterine, lung, non small cell lung, nasopharyngeal carcinoma, neuroblastoma, solid tumor, hematologic malignancy, squamous cell carcinoma, testicular, thyroid, mesothelioma, brain vulval, sarcoma, intestine, oral, endocrine, salivary, spermatocytic seminoma, sporadic medullary thyroid carcinoma, non-proliferating testes cells, cancers related to malignant mast cells, non-Hodgkin's lymphoma, and diffuse large B cell lymphoma.

Exemplary cancers include Acute Lymphoblastic Leukemia, Acute Myeloid Leukemia, Adrenocortical Carcinoma, AIDS-Related Lymphoma, AIDS-Related Malignancies, Anal Cancer, Astrocytoma, Bile Duct Cancer, Extrahepatic, Bladder Cancer; Bone Cancer, Osteosarcoma/Malignant Fibrous Histiocytoma, Brain Stem Glioma, Brain Tumor, Brain Stem Glioma, Cerebellar Astrocytoma, Cerebral Astrocytoma/Malignant Glioma, Ependymoma, Medulloblastoma, Supratentorial Primitive Neuroectodermal Tumors, Visual Pathway and Hypothalamic Glioma; Breast Cancer; Bronchial Adenomas/Carcinoids, Carcinoid Tumor, Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Cerebral Astrocytoma/Malignant Glioma, Cervical Cancer; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer; Cutaneous T-Cell Lymphoma; Endometrial Cancer; Ependymoma, Epithelial Cancer, Ovarian; Esophageal Cancer; Esophageal Cancer; Ewing's Family of Tumors; Extracranial Germ Cell Tumor, Extragonadal Germ Cell Tumor; Extrahepatic Bile Duct Cancer; Eye Cancer, Retinoblastoma; Gallbladder Cancer; Gastric (Stomach) Cancer; Gastric (Stomach) Cancer; Gastrointestinal Carcinoid Tumor; Germ Cell Tumor, Extracranial, Germ Cell Tumor, Extragonadal; Germ Cell Tumor, Ovarian; Gestational Trophoblastic Tumor; Glioma, Glioma, Visual Pathway and Hypothalamic; Hairy Cell Leukemia; Head and Neck Cancer; Hepatocellular (Liver) Cancer; Hodgkin's Lymphoma; Hodgkin's Lymphoma; Hodgkin's Lymphoma During Pregnancy; Hypopharyngeal Cancer; Hypothalamic and Visual Pathway Glioma; Islet Cell Carcinoma (Endocrine Pancreas); Kaposi's Sarcoma; Kidney Cancer; Laryngeal Cancer; Laryngeal Cancer; Leukemia, Acute Lymphoblastic; Leukemia, Acute Lymphoblastic; Leukemia, Acute Myeloid; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoblastic Leukemia, Lymphocytic Leukemia, Chronic; Lymphoma, AIDS-Related; Lymphoma, Central Nervous System (Primary); Lymphoma, Cutaneous T-Cell; Lymphoma, Hodgkin's; Lymphoma, Hodgkin's; Lymphoma, Hodgkin's During Pregnancy; Lymphoma, Non-Hodgkin's; Lymphoma, Non-Hodgkin's; Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma; Malignant Thymoma; Medulloblastoma, Merkel Cell Carcinoma; Mesothelioma, Malignant; Metastatic Squamous Neck Cancer with Occult Primary; Multiple Endocrine Neoplasia Syndrome, Multiple Myeloma/Plasma Cell Neoplasm; Mycosis Fungoides; Myelodysplastic Syndromes; Myelogenous Leukemia, Chronic; Myeloid Leukemia, Myeloma, Multiple; Myeloproliferative Disorders, Chronic; Nasal Cavity and Paranasal Sinus Cancer; Nasopharyngeal Cancer; Nasopharyngeal Cancer; Neuroblastoma; Non-Hodgkin's Lymphoma, Non-Hodgkin's Lymphoma During Pregnancy; Non-Small Cell Lung Cancer; Oral Cancer; Oral Cavity and Lip Cancer; Oropharyngeal Cancer; Osteosarcoma/Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer; Primary Liver Cancer; Prostate Cancer; Rectal Cancer; Renal Cell (Kidney) Cancer; Renal Cell Cancer; Renal Pelvis and Ureter, Transitional Cell Cancer; Retinoblastoma; Rhabdomyosarcoma; Salivary Gland Cancer; Salivary Gland Cancer; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma; Sarcoma, Soft Tissue; Sarcoma, Soft Tissue; Sezary Syndrome; Skin Cancer; Skin Cancer; Skin Cancer (Melanoma); Skin Carcinoma, Merkel Cell; Small Cell Lung Cancer; Small Intestine Cancer; Soft Tissue Sarcoma; Soft Tissue Sarcoma; Squamous Neck Cancer with Occult Primary, Metastatic; Stomach (Gastric) Cancer; Stomach (Gastric) Cancer; Supratentorial Primitive Neuroectodermal Tumors; T-Cell Lymphoma, Cutaneous; Testicular Cancer; Thymoma; Thymoma, Malignant; Thyroid Cancer; Thyroid Cancer; Transitional Cell Cancer of the Renal Pelvis and Ureter; Trophoblastic Tumor, Gestational; Unknown Primary Site, Cancer of; Ureter and Renal Pelvis, Transitional Cell Cancer; Urethral Cancer; Uterine Sarcoma;

Vaginal Cancer; Visual Pathway and Hypothalamic Glioma; Vulvar Cancer; Waldenstrom's Macro globulinemia; and Wilms' Tumor. Metastases of the aforementioned cancers can also be treated in accordance with the methods described herein.

In some embodiments, the tumor is a tumor of the hematopoietic and lymphoid tissues or a tumor that affects the blood, bone marrow, lymph, and lymphatic system. Hematological malignancies include acute lymphoblastic leukemia, acute myelogenous leukemia, chronic lymphocytic leukemia, chronic myelogenous leukemia, acute monocytic leukemia, other leukemias, Hodgkin's lymphomas, and Non-Hodgkin's lymphomas.

In some embodiments, the tumor is a solid tumor. In some embodiments, the solid tumor is locally advanced or metastatic. In some embodiments, the solid tumor is refractory (e.g., resistant) after standard therapy.

Methods described herein can reduce, ameliorate or altogether eliminate the disorder, and/or its associated symptoms, to keep it from becoming worse, to slow the rate of progression, or to minimize the rate of recurrence of the disorder once it has been initially eliminated (i.e., to avoid a relapse). A suitable dose and therapeutic regimen may vary depending upon the specific compounds and/or pharmaceutical compositions used and the mode of delivery of the compounds and/or pharmaceutical compositions. In some embodiments, the method increases the average length of survival, increases the average length of progression-free survival, and/or reduces the rate of recurrence, of subjects treated with the combinations described herein in a statistically significant manner.

In some embodiments, the cancer is lung cancer (e.g., non-small cell lung cancer (NSCLC), e.g., KRAS mutant NSCLC; metastatic cancer), bone cancer, pancreatic cancer, skin cancer, cancer of the head or neck, uterine cancer, ovarian cancer (e.g., unresectable low-grade ovarian, advanced or metastatic ovarian cancer), rectal cancer, cancer of the anal region, stomach cancer, colon cancer, breast cancer (e.g., triple-negative breast cancer (e.g., breast cancer which does not express the genes for the estrogen receptor, progesterone receptor, and Her2/neu)), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney (e.g., Wilms tumor, rhabdoid tumor; nephroma (e.g., mesoblastic nephroma)) or ureter, renal cell carcinoma, carcinoma of the renal pelvis, neoplasms of the central nervous system (CNS), primary CNS lymphoma, spinal axis tumors, brain stem glioma, pituitary adenoma, mesothelioma (e.g., malignant pleural mesothelioma, e.g., surgical resectable malignant pleural mesothelioma) or a combination of one or more of the foregoing cancers. In some embodiments, the cancer is ovarian cancer, pancreatic cancer, non-small cell lung cancer, head and neck cancer. In some embodiments, the cancer is metastatic. In some embodiments, the abnormal cell growth is locally recurring (e.g., the subject has a locally recurrent disease, e.g., cancer).

Methods of the present invention contemplate single as well as multiple administrations of a therapeutically effective amount of a FAK inhibitor in combination with a dual RAF/MEK inhibitor, wherein the FAK inhibitor is VS-6063, or a pharmaceutically acceptable salt thereof, and the dual RAF/MEK inhibitor is CH5126766, or a pharmaceutically acceptable salt thereof. Combinations, e.g., a combination as described herein, e.g., a FAK inhibitor (e.g., VS-6063) in combination with a dual RAF/MEK inhibitor (e.g., CH5126766), can be administered at regular intervals, depending on the nature, severity and extent of the subject's condition. In some embodiments, a combination as described herein, e.g., a FAK inhibitor in combination with a dual RAF/MEK inhibitor, is administered in a single dose, wherein the FAK inhibitor is VS-6063, or a pharmaceutically acceptable salt thereof, and the dual RAF/MEK inhibitor is CH5126766, or a pharmaceutically acceptable salt thereof. In some embodiments, a combination as described herein, e.g., a FAK inhibitor in combination with a dual RAF/MEK inhibitor, is administered in multiple doses, wherein the FAK inhibitor is VS-6063, or a pharmaceutically acceptable salt thereof, and the dual RAF/MEK inhibitor is CH5126766, or a pharmaceutically acceptable salt thereof. In some embodiments, a therapeutically effective amount of a combination as described herein, e.g., a FAK inhibitor (e.g., VS-6063) in combination with a dual RAF/MEK inhibitor (e.g., CH5126766), may be administered orally and periodically at regular intervals (e.g., 1, 2, 3, 4, 5, 6, 7, 8, 9, 10 or more times every 1, 2, 3, 4, 5, or 6 days, or every 1, 2, 3, 4, 5, 6, 7, 8, or 9 weeks, or every 1, 2, 3, 4, 5, 6, 7, 8, 9 months or longer). In some embodiments, a therapeutically effective amount of a combination as described herein, e.g., a FAK inhibitor (e.g., VS-6063) may be administered orally and periodically (e.g., twice daily) in combination with a dual RAF/MEK inhibitor (e.g., CH5126766), that may be administered orally and periodically (e.g., twice a week). In some embodiments, a therapeutically effective amount of a combination as described herein, e.g., a FAK inhibitor (e.g., VS-6063) may be administered orally once daily in combination with a dual RAF/MEK inhibitor (e.g., CH5126766), that may be administered orally and periodically (e.g., twice a week). In some embodiments, a therapeutically effective amount of a combination as described herein, e.g., a FAK inhibitor (e.g., VS-6063) may be administered orally and twice daily in combination with a dual RAF/MEK inhibitor (e.g., CH5126766), that may be administered orally and periodically (e.g., three times a week). VS-6063 and CH5126766 may each be in the form of a pharmaceutically acceptable salt.

In some embodiments, a combination as described herein, e.g., a FAK inhibitor (VS-6063) is administered orally and periodically (e.g., twice daily) in combination with a dual RAF/MEK inhibitor (e.g., CH5126766), that is administered orally and at a predetermined interval (e.g., twice a week), for three weeks, followed by one week off (or an interval of no administration of either FAK inhibitor (e.g., VS-6063) or dual RAF/MEK inhibitor (e.g., CH5126766)), then repeated cyclically (e.g., three weeks on, one week off, three weeks on, one week off, etc.). In some embodiments, CH5126766, or a pharmaceutically acceptable salt thereof, and VS-6063, or a pharmaceutically acceptable salt thereof, are each dosed for at least three weeks. In some embodiments, CH5126766, or a pharmaceutically acceptable salt thereof, and VS-6063, or a pharmaceutically acceptable salt thereof are each dosed for at least four weeks. In some embodiments, CH5126766, or a pharmaceutically acceptable salt thereof, and VS-6063, or a pharmaceutically acceptable salt thereof, are each dosed for at least five weeks. In some embodiments, CH5126766, or a pharmaceutically acceptable salt thereof, and VS-6063, or a pharmaceutically acceptable salt thereof, are each dosed cyclically for four weeks on and then at least one week off.

In other embodiments, CH5126766, or a pharmaceutically acceptable salt thereof, and VS-6063, or a pharmaceutically acceptable salt thereof, are each dosed cyclically for five or six weeks on and then one or two weeks off.

Timing of one week off for VS-6063, or a pharmaceutically acceptable salt thereof, and timing of one week off for CH5126766, or a pharmaceutically acceptable salt thereof, can be simultaneous or different. In a preferred embodiment, timing of one week off for VS-6063, or a pharmaceutically acceptable salt thereof, and timing of one week off for CH5126766, or a pharmaceutically acceptable salt thereof, is simultaneous.

In some embodiments, the dual RAF/MEK inhibitor (e.g., CH5126766) is administered orally once a week. In other embodiments, the dual RAF/MEK inhibitor (e.g., CH5126766) is administered orally twice a week. In other embodiments, the dual RAF/MEK inhibitor (e.g., CH5126766) is administered orally three times a week. In other embodiments, the dual RAF/MEK inhibitor (e.g., CH5126766) is administered orally four times a week. In other embodiments, the dual RAF/MEK inhibitor (e.g., CH5126766) is administered orally five times a week. In other embodiments, the dual RAF/MEK inhibitor (e.g., CH5126766) is administered orally once a day. In other embodiments, the dual RAF/MEK inhibitor (e.g., CH5126766) is administered orally twice a day. CH5126766 may be in the form of a pharmaceutically acceptable salt.

In some embodiments, the FAK inhibitor (e.g., VS-6063) is administered orally twice a day. In some embodiments, the FAK inhibitor (e.g., VS-6063) is administered orally once a day. In some embodiments, the FAK inhibitor (e.g., VS-6063) is administered in a dose of about 100 mg to about 400 mg. In some embodiments, the FAK inhibitor (e.g., VS-6063) is administered in a dose of about 100 mg to about 500 mg. In some embodiments, the FAK inhibitor (e.g., VS-6063) is administered in a dose of about 200 mg to about 500 mg. In some embodiments, the FAK inhibitor (e.g., VS-6063) is administered in a dose of about 200 mg to about 600 mg. In some embodiments, the FAK inhibitor (e.g., VS-6063) is administered in a dose of about 200 mg. In some embodiments, the FAK inhibitor (e.g., VS-6063) is administered in a dose of about 400 mg. It should be appreciated that the FAK inhibitor (e.g., VS-6063) may be administered in a dose at any of the periodic time periods described herein. For example, the FAK inhibitor (e.g., VS-6063) may be administered in a dose of about 200 mg twice daily. The FAK inhibitor (VS-6063) may be administered in a dose of about 400 mg twice daily.

In some embodiments, the dual RAF/MEK inhibitor (e.g., CH5126766) is dosed at about 0.5 mg to about 10 mg. In other embodiments, the dual RAF/MEK inhibitor (e.g., CH5126766) is dosed at about 0.5 mg to about 7 mg. In other embodiments, the dual RAF/MEK inhibitor (e.g., CH5126766) is dosed at about 0.5 mg to about 5 mg. In other embodiments, the dual RAF/MEK inhibitor is dosed at about 1 mg to about 10 mg. In some embodiments, the dual RAF/MEK inhibitor (e.g., CH5126766) is dosed at about 4 mg. In other embodiments, the dual RAF/MEK inhibitor (e.g., CH5126766) is dosed at 3.2 mg. It should be appreciated that the dual RAF/MEK inhibitor (e.g., CH5126766) may be dosed at any of the periodic time frames described herein. For example, the dual RAF/MEK inhibitor (e.g., CH5126766) may be dosed at about 0.5 mg to about 10 mg, twice a week. The dual RAF/MEK inhibitor (e.g., CH5126766) may be dosed at about 4 mg, twice a week. The dual RAF/MEK inhibitor (e.g., CH5126766) may be dosed at 3.2 mg, twice a week. CH5126766 may be in the form of a pharmaceutically acceptable salt.

As described herein, the FAK inhibitor (e.g., VS-6063) may be administered with the dual RAF/MEK inhibitor (e.g., CH5126766). For example, CH5126766, or a pharmaceutically acceptable salt thereof, may be dosed at about 0.5 mg to about 10 mg and VS-6063, or a pharmaceutically acceptable salt thereof, may be dosed at about 100 mg to about 400 mg. CH5126766, or a pharmaceutically acceptable salt thereof, may be dosed at about 3 mg to about 5 mg and VS-6063, or a pharmaceutically acceptable salt thereof, may be dosed at about 100 mg to about 400 mg. CH5126766, or a pharmaceutically acceptable salt thereof, may be dosed at about 3 mg to about 5 mg twice a week and VS-6063, or a pharmaceutically acceptable salt thereof, may be dosed at about 100 mg to about 400 mg twice daily. CH5126766, or a pharmaceutically acceptable salt thereof, may be dosed at about 4.0 mg twice a week and VS-6063, or a pharmaceutically acceptable salt thereof, may be dosed at about 200 mg twice daily. CH5126766, or a pharmaceutically acceptable salt thereof, may be dosed at about 3.2 mg twice a week and VS-6063, or a pharmaceutically acceptable salt thereof, may be dosed at about 200 mg twice daily. CH5126766, or a pharmaceutically acceptable salt thereof, may be dosed at about 3.2 mg twice a week and VS-6063, or a pharmaceutically acceptable salt thereof, may be dosed at about 400 mg twice daily.

In some embodiments, a dual RAF/MEK inhibitor (e.g., CH5126766) is administered according to following steps comprising:
  (a) administering the dual RAF/MEK inhibitor twice a week for 3 weeks,
  (b) pausing administration of said compound or salt for the following 1 week, and
  (c) subsequently repeating steps (a) and (b) at least once.

In some embodiments, the dual RAF/MEK inhibitor (e.g., CH5126766) is administered in the following manner of (R1) or (R2):
  (R1)
    (A1)
    (A1a) The dual RAF/MEK inhibitor (e.g., CH5126766) is administered twice weekly for 3 weeks at a dose of 4 mg per administration,
    (A1b) administration of the dual RAF/MEK inhibitor (e.g., CH5126766) is paused for the following 1 week (namely, 3 weeks on, one week off basis, and total 4 weeks is as 1 cycle), and
    (A1c) steps (A1a) and (A1b) are subsequently repeated at least once; or (R2)
    (A2) First:
    (A2a) the dual RAF/MEK inhibitor (e.g., CH5126766) is administered twice weekly for 3 weeks at a dose of 4 mg per administration,
    (A2b) administration of the dual RAF/MEK inhibitor (e.g., CH5126766) is paused for the following 1 week, and
    (A2c) steps (A2a) and (A2b) are subsequently repeated at least once;
    (B2) following which:
    (B2a) the dual RAF/MEK inhibitor (e.g., CH5126766) is administered twice weekly for 3 weeks at a dose of 3.2 mg per administration,
    (B2b) administration of the dual RAF/MEK inhibitor (e.g., CH5126766) thereof is paused for the following 1 week, and
    (B2c) steps (B2a) and (B2b) are subsequently repeated at least once.

In some embodiments, (i) the 4-week cycle consisting of steps (a) and (b), and (ii) the 4-week cycle consisting of steps (A1a) and (A1b) are repeated two times (8 weeks) to 90 times (approximately 6 years and 11 months), for example, and more specifically, it is repeated 8 times (32 weeks) to 18 times (72 weeks), for example. Even if the number of cycles to be repeated has previously been determined, the number of cycles may be changed based on the judgment of the physician or veterinarian depending on, for example, the condition of the subject. Moreover, administration may even be stopped during the cycle based on the judgment of the physician or veterinarian depending on, for example, the condition of the subject.

In some embodiments, the 4-week cycle consisting of steps (A2a) and (A2b) is repeated two times (8 weeks) to 45 times (approximately 3 years and 5 months), for example, and more specifically, it is repeated 8 times (32 weeks) to 18 times (72 weeks), for example. Even if the number of cycles to be repeated has previously been determined, the number of cycles may be changed based on the judgment of the physician or veterinarian depending on, for example, the condition of the subject. Moreover, administration may even be stopped during the cycle based on the judgment of the physician or veterinarian depending on, for example, the condition of the subject.

In some embodiments, the 4-week cycle consisting of steps (B2a) and (B2b) is repeated two times (8 weeks) to 45 times (approximately 3 years and 5 months), for example, and more specifically, it is repeated 8 times (32 weeks) to 18 times (72 weeks), for example. Even if the number of cycles to be repeated has previously been determined, the number of cycles may be changed based on the judgment of the physician or veterinarian depending on, for example, the condition of the subject. Moreover, administration may even be stopped during the cycle based on the judgment of the physician or veterinarian depending on, for example, the condition of the subject.

In some embodiments, the dose of the dual RAF/MEK inhibitor (e.g., CH5126766) per administration is preferably 3.2 mg or 4 mg. The dose is more preferably 4 mg, which can be reduced to 3.2 mg. The dose of the FAK inhibitor (e.g., VS-6063) per administration is preferably 200 mg or 400 mg. The dose is more preferably 200 mg, which can be increased to 400 mg.

The period during which the dual RAF/MEK inhibitor (e.g., CH5126766) is used in combination with the FAK inhibitor (e.g., VS-6063) may be determined based on the judgment of the physician or veterinarian depending on, for example, the condition of the subject. Also, administration of either or both the dual RAF/MEK inhibitor (e.g., CH5126766) and the FAK inhibitor (e.g., VS-6063) may be stopped based on the judgment of the physician or veterinarian depending on, for example, the condition of the subject.

Compounds

The methods described herein comprise, among other things, administering a FAK inhibitor in combination with a dual RAF/MEK inhibitor to a subject having cancer, wherein the FAK inhibitor is VS-6063, or a pharmaceutically acceptable salt thereof, and the dual RAF/MEK inhibitor is CH5126766, or a pharmaceutically acceptable salt thereof.

VS-6063

Exemplary FAK inhibitors include VS-6063 or a pharmaceutically acceptable salt thereof (e.g., VS-6063 hydrochloride). VS-6063 and related compounds are also disclosed in, e.g., U.S. Pat. No. 7,928,109, the content of which is incorporated herein by reference. VS-6063 is also known as defactinib and PF-04554878, having the following structure:

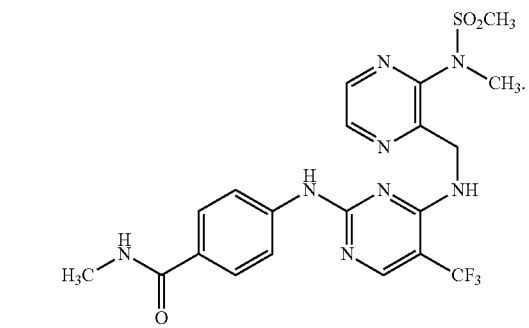 [SMILES: CNC(=O)c1ccc(Nc2ncc(C(F)(F)F)c(NCc3nccnc3N(C)S(C)(=O)=O)n2)cc1]

In some embodiments, VS-6063 can form a pharmaceutically acceptable salt (e.g., VS-6063 hydrochloride). In some embodiments, VS-6063, or a pharmaceutically acceptable salt thereof, is present in a composition in an amount of 5, 10, 11, 12, 12.5, 13, 14, 15, 20, 25, 30, 35, 40, 45, 50, 55, 60% w/w or greater. In some embodiments, VS-6063, or a pharmaceutically acceptable salt thereof, is present in a composition in an amount of from about 5 to about 60% w/w, about 5 to about 50% w/w, about 10 to about 50% w/w, or about 10 to about 40% w/w.

CH5126766

CH5126766 is a dual RAF/MEK inhibitor and is also known as RO5126766. Included herein are methods of using CH5126766, or a pharmaceutically acceptable salt thereof. CH5126766 (free base) is represented by the following formula:

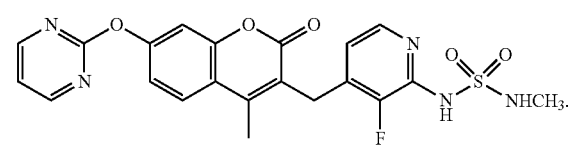 [SMILES: CNS(=O)(=O)Nc1nccc(Cc2c(C)c3ccc(Oc4ncccn4)cc3oc2=O)c1F]

The CH5126766 or pharmaceutically acceptable salt thereof to be used in the present invention is preferably a potassium salt of CH5126766. The potassium salt of CH5126766 is preferably, for example, a salt represented by the following formula:

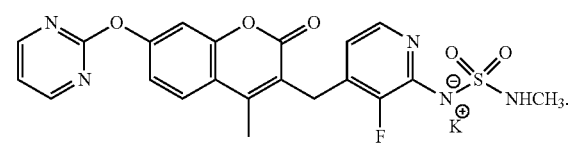 [SMILES: CNS(=O)(=O)[N-]c1nccc(Cc2c(C)c3ccc(Oc4ncccn4)cc3oc2=O)c1F ; [K+]]

For example, CH5126766, and pharmaceutically acceptable salts thereof, are disclosed in WO 2007/091736 and WO 2009/014100 and can be prepared according to the method described in those publications.

Cancer Combination Therapy

In some embodiments, a combination described herein (e.g., VS-6063, or a pharmaceutically acceptable salt thereof, in combination with CH5126766, or a pharmaceutically acceptable salt thereof) is administered together with an additional therapy (e.g., cancer treatment). In one embodiment, a mixture of one or more compounds or pharmaceutical compositions may be administered with the combination described herein, e.g., VS-6063, or a pharmaceutically acceptable salt thereof, in combination with CH5126766, or a pharmaceutically acceptable salt thereof. In yet another embodiment, one or more compounds or compositions (e.g., pharmaceutical compositions) may be administered with the combination described herein, e.g., VS-6063, or a pharmaceutically acceptable salt thereof, in combination with CH5126766, or a pharmaceutically acceptable salt thereof, for the treatment of various diseases, including, for example, cancer.

In various embodiments, combination therapies comprising a compound or pharmaceutical composition described herein may refer to (1) pharmaceutical compositions that comprise one or more compounds in combination with the combination described herein, e.g., VS-6063, or a pharmaceutically acceptable salt thereof, in combination with CH5126766, or a pharmaceutically acceptable salt thereof; and (2) co-administration of one or more compounds or pharmaceutical compositions described herein with the combination described herein, e.g., VS-6063, or a pharmaceutically acceptable salt thereof, in combination with CH5126766, or a pharmaceutically acceptable salt thereof, wherein the compound or pharmaceutical composition described herein have not been formulated in the same compositions. In some embodiments, the combinations described herein (e.g., VS-6063, or a pharmaceutically acceptable salt thereof, in combination with CH5126766, or a pharmaceutically acceptable salt thereof) are administered with an additional treatment (e.g., an additional cancer treatment). In some embodiments, the additional treatment (e.g., an additional cancer treatment) can be administered simultaneously (e.g., at the same time), in the same or in separate compositions, or sequentially. Sequential administration refers to administration of one treatment before (e.g., immediately before, less than 5, 10, 15, 30, 45, 60 minutes; 1, 2, 3, 4, 6, 8, 10, 12, 16, 20, 24, 48, 72, 96 or more hours; 4, 5, 6, 7, 8, 9 or more days; 1, 2, 3, 4, 5, 6, 7, 8 or more weeks before) administration of an additional treatment (e.g., a compound or therapy). The order of administration of the first and secondary compound or therapy can also be reversed. In some embodiments, the FAK inhibitor (e.g., VS-6063) and the dual RAF/MEK inhibitor (e.g., CH5126766) are administered at different periodic time intervals. For example, the FAK inhibitor (e.g., VS-6063) may be administered once daily or twice daily, while the dual RAF/MEK inhibitor (e.g., CH5126766) is administered twice a week, once a week, or every three or four days.

The methods of the invention may be used or administered in combination with one or more additional therapies (e.g., cancer treatment, e.g., surgery, additional drug(s) or therapeutic agents) for the treatment of the disorder/diseases mentioned. The additional therapies (e.g., cancer treatment, e.g., drug(s) or therapeutic agents described herein) can be administered in the same formulation or in separate formulations. If administered in separate formulations, the compounds of the invention may be administered sequentially or simultaneously with the other drug(s).

In addition to being able to be administered in combination with one or more additional therapies (e.g., cancer treatment, e.g., surgery, additional drug(s) or therapeutic agents), methods of the invention may be administered either simultaneously (as a combined preparation) or sequentially in order to achieve a desired effect. This is especially desirable where the therapeutic profile of each compound is different such that the combined effect of the two drugs provides an improved therapeutic result.

Exemplary cancer treatments include, for example, chemotherapy, targeted therapies such as antibody therapies, immunotherapy, and hormonal therapy. Examples of each of these treatments are provided below.

Chemotherapy

In some embodiments, a combination described herein (e.g., VS-6063, or a pharmaceutically acceptable salt thereof, in combination with CH5126766, or a pharmaceutically acceptable salt thereof) is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer chemotherapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time or sequentially. Often, two or more chemotherapy agents are used as combination chemotherapy. In some embodiments, the chemotherapy agents (including combination chemotherapy)

can be used in combination with a combination described herein (e.g., a FAK inhibitor in combination with a dual RAF/MEK inhibitor).

Targeted Therapy

In some embodiments, a combination described herein (e.g., VS-6063, or a pharmaceutically acceptable salt thereof, in combination with CH5126766, or a pharmaceutically acceptable salt thereof) is administered with a targeted therapy. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erolotinib, imatinib, gefitinib, lapatinib, Lestaurtinib, Nilotinib, Semaxanib, Sorafenib, Sunitinib, and Vandetanib, and also cyclin-depdendent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Ctuximab, Panitumumab, Trastuzumab, Alemtuzumab, Bevacizumab, Edrecolomab, and Gemtuzumab. Exemplary fusion proteins include Aflibercept and Denileukin diftitox. Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a combination described herein (e.g., VS-6063, or a pharmaceutically acceptable salt thereof, in combination with CH5126766, or a pharmaceutically acceptable salt thereof) is administered with an immunotherapy. Cancer immunotherapy refers to a diverse set of therapeutic strategies designed to induce the patient's own immune system to fight the tumor. Contemporary methods for generating an immune response against tumors include use of IL-2 and intravesicular BCG immunotherapy for bladder cancer, and use of interferons and other cytokines to induce an immune response in subjects with renal cell carcinoma, melanoma, multiple myeloma, chronic myelogenous leukemia and hairy cell leukemia.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a combination as described herein, e.g., VS-6063, or a pharmaceutically acceptable salt thereof, in combination with CH5126766, or a pharmaceutically acceptable salt thereof.

In some embodiments, the immunotherapeutic agent is a compound (e.g., a ligand, an antibody) that inhibits the immune checkpoint blockade pathway. Cancer immunotherapy refers to the use of the immune system to treat cancer. Three main groups of immunotherapy used to treat cancer includes cell-based, antibody-based, and cytokine therapies. All groups exploit cancer cells' display of subtly different structures (e.g., molecular structure, antigens, proteins, molecules, carbohydrates) on their surface that can be detected by the immune system. Cancer immunotherapy (i.e., anti-tumor immunotherapy or anti-tumor immunotherapeutics) include immune checkpoint antibodies (e.g., PD-1 antibodies, PD-L1 antibodies, PD-L2 antibodies, CTLA-4 antibodies, TIM3 antibodies, LAG3 antibodies, TIGIT antibodies) and cancer vaccines (i.e., anti-tumor vaccines).

In some embodiments, the immunotherapeutic agent is an anti-CTLA-4 antibody (e.g., ipilimumab, tremelimumab), anti-TIM3, anti-LAG3 or anti-TIGIT. In some embodiments, the immunotherapeutic agent is an anti-PD-1 ligand (e.g., PD-L1 (e.g., B7-HI or CD274); or PD-L2 (e.g., B7-DC or CD273)). In some embodiments, the immunotherapeutic agent is an anti-PD-1 antibody (e.g., anti-PD-1 or anti-PD-L1, (e.g., nivolumab (i.e., MDX-1106, BMS-936558, ONO-4538); CT-011; AMP-224; pembrolizumab; pidilizumab; or MK-3475). In some embodiments, the immunotherapeutic agent is an anti-PD-L1 antibody (e.g., BMS936559 (i.e., MDX-1105); MEDI4736; MSB0010718C (avelumab); or MPDL-3280A). In some embodiments, the immunotherapeutic agent is a cell-based therapy. In some embodiments, the cell-based therapy is a CAR-T therapy. In some embodiments, the immunotherapeutic agent is a co-stimulatory antibody (e.g., anti-4-1BB, anti-OX40, anti-GITR, anti-CD27, anti-CD40). In some embodiments, the method further comprises administering an additional chemotherapeutic agent or radiation therapy. In some embodiments, the method further comprises administering a cytotoxic agent. In some embodiments, the cytotoxic agent is gemcitabine or paclitaxel (e.g., nab-paclitaxel). In some embodiments, the immunotherapeutic agent is a co-stimulatory antibody (e.g., anti-4-1BB, anti-OX40, anti-GITR, anti-CD27, anti-CD40).

Anti-Inflammatory Agents

In some embodiments, a combination described herein (e.g., VS-6063, or a pharmaceutically acceptable salt thereof, in combination with CH5126766, or a pharmaceutically acceptable salt thereof) can be administered with an anti-inflammatory agent. Anti-inflammatory agents include non-steroidal anti-inflammatory agents (e.g., Salicylates (Aspirin (acetylsalicylic acid), Diflunisal, Salsalate), Propionic acid derivatives (Ibuprofen, Naproxen, Fenoprofen, Ketoprofen, Flurbiprofen, Oxaprozin, Loxoprofen), Acetic acid derivatives (Indomethacin, Sulindac, Etodolac, Ketorolac, Diclofenac, Nabumetone), Enolic acid (Oxicam) derivatives (Piroxicam, Meloxicam, Tenoxicam, Droxicam, Lornoxicam, Isoxicam), Fenamic acid derivatives (Fenamates) (Mefenamic acid, Meclofenamic acid, Flufenamic acid, Tolfenamic acid), Selective COX-2 inhibitors (Coxibs) (Celecoxib), Sulphonanilides (Nimesulide). Steriods (e.g., Hydrocortisone (Cortisol), Cortisone acetate, Prednisone, Prednisolone, Methylprednisolone, Dexamethasone, Betamethasone, Triamcinolone, Beclometasone, Fludrocortisone acetate, Deoxycorticosterone acetate, Aldosterone).

Analgesic Agents

In some embodiments, a combination described herein (e.g VS-6063, or a pharmaceutically acceptable salt thereof, in combination with CH5126766, or a pharmaceutically acceptable salt thereof) can be administered with analgesic agents. Analgesics include opiates (e.g., morphine, codeine, oxycodone, hydrocodone, dihydromorphine, pethidine, buprenorphine, tramadol, venlafaxine), paracetomal and non-steroidal anti-inflammatory agents (e.g., Salicylates (Aspirin (acetylsalicylic acid), Diflunisal, Salsalate), Propionic acid derivatives (Ibuprofen, Naproxen, Fenoprofen, Ketoprofen, Flurbiprofen, Oxaprozin, Loxoprofen), Acetic acid derivatives (Indomethacin, Sulindac, Etodolac, Ketorolac, Diclofenac, Nabumetone), Enolic acid (Oxicam) derivatives (Piroxicam, Meloxicam, Tenoxicam, Droxicam, Lornoxicam, Isoxicam), Fenamic acid derivatives (Fenamates)

(Mefenamic acid, Meclofenamic acid, Flufenamic acid, Tolfenamic acid), Selective COX-2 inhibitors (Coxibs) (Celecoxib), Sulphonanilides (Nimesulide).

Antiemetic Agents

In some embodiments, a combination described herein (e.g., VS-6063, or a pharmaceutically acceptable salt thereof, in combination with CH5126766, or a pharmaceutically acceptable salt thereof) can be administered with an antiemetic agent. Antiemetic agents include 5-HT3 receptor antagonists (Dolasetron (Anzemet), Granisetron (Kytril, Sancuso), Ondansetron (Zofran), Tropisetron (Navoban), Palonosetron (Aloxi), Mirtazapine (Remeron)), Dopamine antagonists (Domperidone, Olanzapine, Droperidol, Haloperidol, Chlorpromazine, Promethazine, Prochlorperazine, Metoclopramide (Reglan), Alizapride, Prochlorperazine (Compazine, Stemzine, Buccastem, Stemetil, Phenotil), NK1 receptor antagonist (Aprepitant (Emend), Antihistamines (Cyclizine, Diphenhydramine (Benadryl), Dimenhydrinate (Gravol, Dramamine), Meclozine (Bonine, Antivert), Promethazine (Pentazine, Phenergan, Promacot), Hydroxyzine), benzodiazapines (Lorazepam, Midazolam), Anticholinergics (hyoscine), steriods (Dexamethasone).

Hormonal Therapy

In some embodiments, a combination described herein (e.g., VS-6063, or a pharmaceutically acceptable salt thereof, in combination with CH5126766, or a pharmaceutically acceptable salt thereof) is administered with a hormonal therapy. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a combination described herein (e.g., VS-6063, or a pharmaceutically acceptable salt thereof, in combination with CH5126766, or a pharmaceutically acceptable salt thereof).

Radiation Therapy

In some embodiments, a combination described herein (e.g., VS-6063, or a pharmaceutically acceptable salt thereof, in combination with CH5126766, or a pharmaceutically acceptable salt thereof) can be used in combination with directed energy or particle, or radioisotope treatments, e.g., radiation therapies, e.g., radiation oncology, for the treatment of proliferative disease, e.g., cancer, e.g., cancer associated with cancer stem cells. The methods of the invention may be administered to a subject simultaneously or sequentially along with the directed energy or particle, or radioisotope treatments. For example, the methods of the invention may be administered before, during, or after the directed energy or particle, or radioisotope treatment, or a combination thereof. The directed energy or particle therapy may comprise total body irradiation, local body irradiation, or point irradiation. The directed energy or particle may originate from an accelerator, synchrotron, nuclear reaction, vacuum tube, laser, or from a radioisotope. The therapy may comprise external beam radiation therapy, teletherapy, brachytherapy, sealed source radiation therapy, systemic radioisotope therapy, or unsealed source radiotherapy. The therapy may comprise ingestion of, or placement in proximity to, a radioisotope, e.g., radioactive iodine, cobalt, cesium, potassium, bromine, fluorine, carbon. External beam radiation may comprise exposure to directed alpha particles, electrons (e.g., beta particles), protons, neutrons, positrons, or photons (e.g., radiowave, millimeter wave, microwave, infrared, visible, ultraviolet, X-ray, or gamma-ray photons). The radiation may be directed at any portion of the subject in need of treatment.

Surgery

In some embodiments, a combination described herein (e.g., VS-6063, or a pharmaceutically acceptable salt thereof, in combination with CH5126766, or a pharmaceutically acceptable salt thereof) can be used in combination with surgery, e.g., surgical exploration, intervention, biopsy, for the treatment of proliferative disease, e.g., cancer, e.g., cancer associated with cancer stem cells. The methods of the invention may be administered to a subject simultaneously or sequentially along with the surgery. For example, the methods of the invention may be administered before (pre-operative), during, or after (post-operative) the surgery, or a combination thereof. A FAK inhibitor (e.g., VS-6063) may be administered before (pre-operative) the surgery and a dual RAF/MEK inhibitor (e.g., CH5126766) may be administered during, or after (post-operative) the surgery. Alternatively, a dual RAF/MEK inhibitor (e.g., CH5126766) may be administered before (pre-operative) the surgery and a FAK inhibitor (e.g., VS-6063) may be administered during, or after (post-operative) the surgery. The surgery may be a biopsy during which one or more cells are collected for further analysis. The biopsy may be accomplished, for example, with a scalpel, a needle, a catheter, an endoscope, a spatula, or scissors. The biopsy may be an excisional biopsy, an incisional biopsy, a core biopsy, or a needle biopsy, e.g., a needle aspiration biopsy. The surgery may involve the removal of localized tissues suspected to be or identified as being cancerous. For example, the procedure may involve the removal of a cancerous lesion, lump, polyp, or mole. The procedure may involve the removal of larger amounts of tissue, such as breast, bone, skin, fat, or muscle. The procedure may involve removal of part of, or the entirety of, an organ or node, for example, lung, throat, tongue, bladder, cervix, ovary, testicle, lymph node, liver, pancreas, brain, eye, kidney, gallbladder, stomach, colon, rectum, or intestine. In one embodiment, the cancer is breast cancer, e.g., triple negative breast cancer, and the surgery is a mastectomy or lumpectomy.

First-Line Therapy

In some embodiments, described herein is a method of treating a human subject having cancer, wherein the subject has failed (e.g., relapsed from, insensitive to, received no or little benefit from) first-line treatment (e.g., first-line therapy for cancer). The present invention also describes a method of treating a human subject having cancer, wherein the methods of the invention are administered with an additional agent. In some embodiments, the additional agent is a first-line therapy for cancer.

First-line therapy is typically the first treatment given for a disease (e.g., cancer as described herein). It is often part of a standard set of treatments, such as surgery followed by chemotherapy and radiation. When used by itself, first-line therapy is generally the one accepted as the best treatment. If it does not cure the disease or it causes severe side effects, other treatment(s) may be added or used instead. First-line therapy is also called induction therapy, primary therapy, and primary treatment.

For example, first-line-therapy, e.g., for Hodgkin lymphoma may include: Adcetris (Brentuximab Vedotin), Adriamycin PFS (Doxorubicin Hydrochloride), Adriamycin RDF (Doxorubicin Hydrochloride), Ambochlorin (Chlorambucil), Amboclorin (Chlorambucil), Blenoxane (Bleomycin), Bleomycin, Brentuximab Vedotin, Chlorambucil, Clafen (Cyclophosphamide), Cyclophosphamide, Cytoxan (Cyclophosphamide), Dacarbazine, Doxorubicin Hydrochloride, DTIC-Dome (Dacarbazine), Leukeran (Chlorambucil), Linfolizin (Chlorambucil), Lomustine, Matulane (Procarbazine Hydrochloride), Neosar (Cyclophosphamide), Procarbazine Hydrochloride, Velban (Vinblastine Sulfate), Velsar (Vinblastine Sulfate), Vinblastine Sulfate, Vincasar PFS (Vincristine Sulfate), and Vincristine Sulfate.

In some embodiments, first-line-therapy, e.g., for Hodgkin lymphoma comprises administration of a combination of therapeutic agents, e.g., therapeutic agents as described herein. For example, the combination may comprise Doxorubicin Hydrochloride (Adriamycin), Bleomycin, Vinblastine Sulfate, and Dacarbazine (i.e., ABVD). As another example, the combination may comprise Doxorubicin Hydrochloride (Adriamycin), Bleomycin, Vinblastine Sulfate, and Etoposide (i.e., ABVE). In some embodiments, the combination comprises Doxorubicin Hydrochloride (Adriamycin), Bleomycin, Vinblastine Sulfate, Etoposide, Prednisone, and Cyclophosphamide (i.e., ABVE-PC). In some embodiments, the combination comprises Vincristine Sulfate, Doxorubicin Hydrochloride (Adriamycin), Methotrexate, and Prednisone (i.e., VAMP).

Approved therapeutic agents and combinations for different types of cancer can be found on the National Cancer Institute at the National Institutes of Health Cancer website at http://www.cancer.gov/cancertopics/druginfo/drug-page-index.

Second-Line Therapy

In some embodiments, described herein is a method of treating a human subject having cancer, wherein the subject has failed (e.g., relapsed from, insensitive to, received no or little benefit from) second-line or more treatment (e.g., second-line therapy for cancer, or third-line therapy for cancer). The present invention also describes a method of treating a human subject having cancer, wherein the methods of the invention are administered with an additional agent. In some embodiments, the additional agent is a first or second line therapy for cancer. Second-line therapy generally refers to treatment that is given when initial treatment (e.g., first-line therapy) does not achieve a desired result, e.g., does not work, is not efficacious; stops working. Second-line therapy is typically considered or given when a subject does not respond or develops a resistance to initial treatment (e.g., first-line therapy). For example, second-line therapy is typically considered or given to a subject with relapsed or refractory disease.

Administration and Dosage

The combinations of this invention may be administered orally, parenterally, topically, rectally, or via an implanted reservoir, preferably by oral administration or administration by injection. In some cases, the pH of the composition (e.g., pharmaceutical composition) may be adjusted with pharmaceutically acceptable acids, bases or buffers to enhance the stability or efficacy of the composition.

In some embodiments, the subject is administered the composition (e.g., pharmaceutical composition) orally. In some embodiments the composition (e.g., pharmaceutical composition) is orally administered in any orally acceptable dosage form including liqui-gel, tablets or capsules, syrups, emulsions and aqueous suspensions. Liqui-gels may include gelatins, plasticisers, and/or opacifiers, as needed to achieve a suitable consistency and may be coated with enteric coatings that are approved for use, e.g., shellacs. Additional thickening agents, for example gums, e.g., xanthum gum, starches, e.g., corn starch, or glutens may be added to achieve a desired consistency of the composition (e.g., pharmaceutical composition) when used as an oral dosage. If desired, certain sweetening and/or flavoring and/or coloring agents may be added.

In some embodiments, the subject is administered the composition (e.g., pharmaceutical composition) in a form suitable for oral administration such as a tablet, capsule, pill, powder, sustained release formulations, solution, and suspension. The composition (e.g., pharmaceutical composition) may be in unit dosage forms suitable for single administration of precise dosages. Pharmaceutical compositions may comprise, in addition to a compound as described herein (e.g., a FAK inhibitor (e.g., VS-6063); a dual RAF/MEK inhibitor (e.g., CH5126766)), a pharmaceutically acceptable carrier, and may optionally further comprise one or more pharmaceutically acceptable excipients, such as, for example, excipients, lubricants (coating agents), binders, disintegrants, stabilizers, flavoring agents, bases, dispersants, diluents, surfactants, emulsifiers, and the like. In addition, the tablet may include other medicinal or pharmaceutical agents, carriers, and or adjuvants.

Examples of excipients include starches (starch, potato starch, maize starch and the like), lactose, crystalline cellulose, and calcium hydrogen phosphate.

Examples of lubricants (coating agents) include ethyl cellulose, hydroxypropyl cellulose, hydroxypropylmethyl cellulose, shellac, talc, carnauba wax, and paraffin.

Examples of binders include polyvinylpyrrolidone and macrogol, as well as the same compounds as mentioned for the excipient.

Examples of disintegrants include chemically modified starches and celluloses, such as croscarmellose sodium, sodium carboxymethyl starch, and crosslinked polyvinylpyrrolidone, as well as the same compounds as mentioned for the excipient.

Examples of stabilizers include: paraoxybenzoic acid esters such as methylparaben and propylparaben; benzalkonium chloride; phenols such as phenol and cresol; thimerosal; dehydroacetic acid; and sorbic acid.

Examples of flavoring agents include sweeteners, acidulants and fragrances which are commonly used.

Examples of bases include: fats such as lard; vegetable oils such as olive oil and sesame oil; higher alcohols such as stearyl alcohol and cetanol; animal oils; lanolin acid; vaseline; paraffins; bentonite; glycerine; and glycol oils.

Examples of dispersants include cellulose derivatives (gum arabic, tragacanth, methyl cellulose and the like), stearic acid polyesters, sorbitan sesquioleate, aluminum monostearate, sodium alginate, polysorbates, and sorbitan fatty acid esters.

Examples of solvents and diluents in liquid formulations include phenol, chlorocresol, purified water and distilled water.

Examples of surfactants and emulsifiers include polysorbate 80, polyoxyl 40 stearate, and lauromacrogol.

The preferred percentage of the RAF/MEK inhibitor (e.g., CH5126766) or the FAK (e.g., VS-6063) inhibitor contained in the formulation will differ depending on the dosage form, but it is generally 0.01% to 100% by weight with respect to the total weight of the formulation.

The content of the RAF/MEK inhibitor (e.g., CH5126766) in the formulation may be set as appropriate for the predetermined dosage. The preferred content is 0.01 mg to 10 mg, for example; for a capsule, it may be 0.1 mg to 4 mg, for example. A more preferred content is 0.8 mg, for example.

Exemplary pharmaceutical compositions include compressed tablets (e.g., directly compressed tablets), e.g., comprising a FAK inhibitor (e.g., VS-6063); or a dual RAF/MEK inhibitor (e.g., CH5126766).

Tablets are also provided comprising the active or therapeutic ingredient (e.g., compound as described herein (e.g., a FAK inhibitor (e.g., VS-6063) and a dual RAF/MEK inhibitor (e.g., CH5126766))). In addition to the active or therapeutic ingredients, tablets may contain a number of inert materials such as carriers. Pharmaceutically acceptable carriers can be sterile liquids, such as water and oils, including those of petroleum, vegetable or synthetic origin, such as peanut oil, sesame oil and the like. Saline solutions and aqueous dextrose can also be employed as liquid carriers. Oral dosage forms for use in accordance with the present invention thus may be formulated in conventional manner using one or more pharmaceutically acceptable carriers comprising excipients and auxiliaries, which facilitate processing of the active ingredients into preparations which, can be used pharmaceutically.

Excipients can impart good powder flow and compression characteristics to the material being compressed. Examples of excipients are described, for example, in the Handbook of Pharmaceutical Excipients ($5^{th}$ edition), Edited by Raymond C Rowe, Paul J. Sheskey, and Sian C. Owen; Publisher: Pharmaceutical Press.

For oral administration, the active ingredients, e.g., the compound as described herein (e.g., a FAK inhibitor (e.g., VS-6063); a dual RAF/MEK inhibitor (e.g., CH5126766)), can be formulated readily by combining the active ingredients with pharmaceutically acceptable carriers well known in the art. Such carriers enable the active ingredients of the invention to be formulated as tablets, pills, capsules, liquids, gels, syrups, slurries, powders or granules, suspensions or solutions in water or nonaqueous media, and the like, for oral ingestion by a subject. Pharmacological preparations for oral use can be made using a solid excipient, optionally grinding the resulting mixture, and processing the mixture of granules, after adding suitable auxiliaries if desired, to obtain, for example, tablets. Suitable excipients such as diluents, binders or disintegrants may be desirable. Also, a FAK inhibitor (e.g., VS-6063) and a dual RAF/MEK inhibitor (e.g., CH5126766) can be formulated separately according to the method described above.

The dosage may vary depending upon the dosage form employed and the route of administration utilized. The exact formulation, route of administration and dosage can be chosen by the individual physician in view of the patient's condition. (See, e.g., Fingl, et al., 1975, in "The Pharmacological Basis of Therapeutics"). Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician. A course of therapy can comprise one or more separate administrations of a compound as described herein (e.g., VS-6063, or a pharmaceutically acceptable salt thereof, and/or CH5126766, or a pharmaceutically acceptable salt thereof).

Oral dosage forms may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

The dosing regimen used in the present invention makes it possible to administer the dual RAF/MEK inhibitor (e.g., CH5126766) in combination with the FAK inhibitor (e.g., VS-6063) for long periods while minimizing side effects and maintaining the drug's efficacy. In addition, the dosing regimen and the combination make it possible to treat or prevent cell proliferative disorders, particularly cancer, while minimizing the burden on patients.

Definitions

As used herein, the articles "a" and "an" refer to one or to more than one (e.g., at least one) of the grammatical object of the article.

"About" and "approximately", as used herein, refer to an acceptable degree of error for the quantity measured given the nature or precision of the measurements. Exemplary degrees of error are within 20 percent (%), typically, within 10%, and more typically, within 5% of a given value or range of values.

As used herein, an amount of a compound effective to treat a disease or disorder described herein (e.g., abnormal cell growth, e.g., cancer (e.g., a cancer described herein)), "effective amount" or "effective course" refers to an amount of the compound which is effective, upon single or multiple dose administration(s) to a subject, in treating a subject, or in curing, alleviating, relieving or improving a subject with a disease or disorder described herein (e.g., abnormal cell growth, e.g., cancer (e.g., a cancer described herein)) beyond that expected in the absence of such treatment (e.g., placebo treatment).

The term "pharmaceutically acceptable", as used herein, refers to a compound or carrier (e.g., excipient) that may be administered to a subject, together with a compound described herein (e.g., VS-6063, or a pharmaceutically acceptable salt thereof, and/or CH5126766, or a pharmaceutically acceptable salt thereof), and which does not destroy the pharmacological activity thereof and is nontoxic when administered in doses sufficient to deliver a therapeutic amount of the compound.

The term, "pharmaceutically acceptable salts", as used herein, refers to derivatives of a compound described herein (e.g., VS-6063, or a pharmaceutically acceptable salt thereof, and/or CH5126766, or a pharmaceutically acceptable salt thereof), wherein the compound is modified by converting an existing acid or base moiety to its salt form. Examples of pharmaceutically acceptable salts include mineral or organic acid salts of basic residues such as amines; alkali or organic salts of acidic residues such as carboxylic acids; and the like. Pharmaceutically acceptable salts of the disclosure include the conventional non-toxic salts of a compound described herein, formed, for example, from non-toxic inorganic or organic acids. Pharmaceutically acceptable salts of the disclosure can be synthesized from a compound described herein (e.g., VS-6063, or a pharmaceutically acceptable salt thereof, and/or CH5126766, or a pharmaceutically acceptable salt thereof), which contains a basic or acidic moiety by conventional chemical methods.

Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety. Examples of pharmaceutically acceptable salts also include: inorganic acid salts such as hydrochlorides, hydrobromides, hydroiodides, sulfates and phosphates; sulfonates such as methanesulfonates, benzenesulfonates and toluenesulfonates; carboxylates such as formates, acetates, oxalates, maleates, fumarates, citrates, malates, succinates, malonates, gluconates, mandelates, benzoates, salicylates, fluoroacetates, trifluoroacetates, tartrates, propionates and glutarates; alkali metal salts such as lithium salts, sodium salts, potassium salts, cesium salts and rubidium salts; alkaline earth metal salts such as magnesium salts and calcium salts; and ammonium salts such as ammonium salts, alkylammonium salts, dialkylammonium salts, trialkylammonium salts and tetraalkylammonium salts.

The term, "oral dosage form", as used herein, refers to a composition or medium used to administer an agent, e.g., a therapeutic agent, e.g., a compound as described herein, to a subject. Typically, an oral dosage form is administered via the mouth, however, "oral dosage form" is intended to cover any substance which is administered to a subject and is absorbed across a membrane, e.g., a mucosal membrane, of the gastrointestinal tract, including, e.g., the mouth, esophagus, stomach, small intestine, large intestine, and colon. For example, "oral dosage form" covers a solution which is administered through a feeding tube into the stomach.

The term, "treat" or "treatment", as used herein, refers to the application or administration of a compound, alone or in combination with, an additional agent to a subject, e.g., a subject who has a disease or disorder described herein (e.g., abnormal cell growth, e.g., cancer (e.g., a cancer described herein)) or is suffering from a disease or disorder described herein (e.g., abnormal cell growth, e.g., cancer (e.g., a cancer described herein)), a symptom of a disease or disorder described herein (e.g., abnormal cell growth, e.g., cancer (e.g., a cancer described herein)), or a predisposition toward a disease or disorder described herein (e.g., abnormal cell growth, e.g., cancer (e.g., a cancer described herein)), with the purpose to cure, heal, alleviate, relieve, alter, remedy, ameliorate, improve or affect the disease or disorder described herein (e.g., abnormal cell growth, e.g., cancer (e.g., a cancer described herein)).

The phrase, "in combination with", and the terms "co-administration", "co-administering", or "co-providing", as used herein in the context of the administration of a compound described herein or a therapy described herein, means that two (or more) different compounds or therapies are delivered to the subject during the course of the subject's affliction with the disease or disorder (e.g., a cancer), e.g., two (or more) different compounds or therapies are delivered to the subject after the subject has been diagnosed with the disease or disorder (e.g., a disease or disorder as described herein, e.g., cancer) and before the disease or disorder has been cured or eliminated or treatment has ceased for other reasons. Combinations can achieve synergistic results, i.e., greater than additive results, e.g., at least 20, 50, 70, or 100% greater than additive.

As used herein, the phrase "synergistic effect" refers to a greater than additive effect (e.g., therapeutic effect) of two or more compounds or compositions. An exemplary synergistic effect includes administration of an amount of a FAK inhibitor (e.g., VS-6063) used (e.g., administered) in combination with an amount of a dual RAF/MEK inhibitor (e.g., CH5126766) that results in a therapeutic effect that is greater than the additive therapeutic effect of each inhibitor used alone.

"Course of therapy", as referred to herein, comprises one or more separate administrations of a therapeutic agent. A course of therapy can comprise one or more cycles of a therapeutic agent.

A "cycle", as used herein in the context of a cycle of administration of a drug, refers to a period of time for which a drug is administered to a patient. Preferably, one cycle is equal to four weeks.

Numerous ranges, e.g., ranges for the amount of a drug administered per day, are provided herein. In some embodiments, the range includes both endpoints. In other embodiments, the range excludes one or both endpoints. By way of example, the range can exclude the lower endpoint. Thus, in such an embodiment, a range of 100 to 400 mg/day, excluding the lower endpoint, would cover an amount greater than 100 that is less than or equal to 400 mg/day.

As used herein, the term "subject" is intended to include human and non-human animals. In some embodiments, the subject is a human. Exemplary human subjects include a human subject having a disease or disorder described herein (e.g., abnormal cell growth, e.g., cancer (e.g., a cancer described herein)) or is suffering from a disease or disorder described herein (e.g., abnormal cell growth, e.g., cancer (e.g., a cancer described herein)). The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

The phrase "twice a week" means that the dual RAF/MEK inhibitor (e.g., CH5126766) is administered two times during a one-week period. Administration may be performed twice on the same day, or once a day on different days (which may be consecutive), but it is preferably performed on different days. More preferably, administration is performed on the 1st and 4th days or the 2nd and 5th days of the period, for example, so that the dual RAF/MEK inhibitor (e.g., CH5126766) is administered at dose intervals as uniform as possible, i.e., at dose intervals of 3 to 4 days. The one-week period may start on a Monday, for example, or it may start on a Tuesday, for example. When two administrations are performed on different days, each may be performed at any time of day, but they are preferably performed at the same time of day (for example, after breakfast).

EXAMPLES

The representative examples that follow are intended to help illustrate the invention, and are not intended to, nor should they be construed to, limit the scope of the invention.

In Examples 1 and 2 below and Table 1 to 4 below, "CH5126766" means a potassium salt of CH5126766 and "VS-6063" means VS-6063 hydrochloride.

Example 1. Phase I Trial of the Combination of VS-6063 (a FAK Inhibitor) and CH5126766 (a Dual RAF/MEK Inhibitor) in Patients with Advanced Solid Tumours [NCT03875820]

Methods

The study explored a dose escalation cohort, a mandatory biopsy cohort and expansion cohorts. CH5126766 was dosed twice a week and VS-6063 was dosed twice daily (BD). Each cycle consisted of dosing with both drugs on 3 weeks on one week off basis (1 cycle=4 weeks). The escalation cohort explored 3 dose levels. Dose level 1 included a schedule of 3.2 mg CH5126766+200 mg BD of VS-6063, Dose level 2A 4 mg CH5126766+200 mg BD of VS-6063 and Dose level 2B 3.2 mg CH5126766+400 mg BD of VS-6063. The maximum dose at which no more than 1 of 6 patients at the same dose level experience a drug related toxicity (DLT) as specified in the protocol was determined. The safety and toxicity profile of CH5126766 and VS-6063 were assessed. The causality and grading severity of each adverse event by National Cancer Institute (NCI) Common Terminology Criteria for Adverse Events (CTCAE) version 4.0 were determined. Disease response by RECIST criteria version 1.1 were examined every two cycles. Serum tumor marker(s) were also examined for the eligible patients. Also the data related to progression free survival were collected.

Finding

The most common side effects in the dose escalation were rash and non-dose limiting nausea and hyperbilirubinemia. No DLTs were observed in both cohorts 1 and 2A. DLTs of Grade 2 rash requiring dose interruption or dose reduction in Cycle 1 were seen in cohort 2B (corresponding to dose level 2B), thus cohort 2A (corresponding to dose level 2A) was declared as the recommended phase 2 dose (R2PD). Ovarian cancer with KRAS mutations (3 of low grade serous, and 1 of mucinous adenocarcinoma), a KRAS mutant lung cancer evaluable for response have had a partial response. Two NRAS mutated colon/rectal cancers have been treated showing more than a 50% reduction in CEA levels with Stable disease. A pancreatic cancer with KRAS mutant showed minor response (−19%, −14%, and −11% at Cycles 2, 4, and 6, respectively) with showing more than a 50% reduction in CA19-9 level.

Representative results of disease response, serum tumor marker(s), and treatment duration obtained so far were shown in Example 2.

Conclusions

The combination of CH5126766 and VS-6063 is tolerable and highly active in patients with ovarian cancer and other tumours with KRAS and/or NRAS mutations.

Example 2. Combination of CH5126766 and VS-6063 in Patients with Advanced Solid Tumors In Tables 1 to 4 below, "CH" represents a potassium salt of CH5126766, which was administered twice weekly, and "VS" represents VS-6063 hydrochloride, which was administered twice per day (BID). Each cycle consisted of dosing with both drugs on 3 weeks on one week off basis (1 cycle=4 weeks). "PR" represents Partial Response; "SD" represents Stable Disease; and "N/A" represents not available.

TABLE 1

Combination of CH5126766 and VS-6063 administered to patients with ovarian cancer

| Trial ID Dose level | Tumor types | mutation | First dose | Best Response | % tumor size | Overall Response | CA125 level % | Response | Status** |
|---|---|---|---|---|---|---|---|---|---|
| 101001 CH: 3.2 mg VS: 200 mg | Low grade serous ovarian carcinoma | KRAS | 19 Dec. 2017 | PR | −43 (Cycle 12) | PR | −75 (Cycle 6) | PR | On study (in Cycle 20) |
| 101002 CH: 3.2 mg VS: 200 mg | Low grade serous papillary ovarian carcinoma | ATM & KRAS | 30 Jan. 2018 | PR | −57 (Cycle 12) | PR | −93 (Cycle 12) | PR | On study (in Cycle 19) |
| 101008 CH: 4.0 mg VS: 200 mg | Mucinous adenocarcinoma ovarian | KRAS | 3 Apr. 2018 | PR | −63 (Cycle 6) | PR | N/A | N/A | Off study after Cycle 15 |
| 101009 CH: 4.0 mg VS: 200 mg | Low grade serous ovarian adenocarcinoma | KRAS, CA125 secretor | 24 Apr. 2018 | PR | −55 (Cycle 10) | PR | −94 (Cycle 10) | PR | On study (in Cycle 16) |

**Data cut off 18 Jun. 2019

TABLE 2

Combination of CH5126766 and VS-6063 administered to patients with NSCLC

| Trial ID Dose level | Tumor types | mutation | First dose | Best Response | % tumor size | Overall Response | Status** |
|---|---|---|---|---|---|---|---|
| 101010 CH: 4.0 mg VS: 200 mg | NSCLC | KRAS | 5 Jun. 2018 | PR | −46 (Cycle 2) | PR | Off study after Cycle 4 |

**Data cut off 18 Jun. 2019

TABLE 3

Combination of CH5126766 and VS-6063 administered to patients with colorectal cancer

| Trial ID Dose level | Tumor types | mutation | First dose | Best Response | % tumor size | Overall Response | CEA level % | CA19-9 level % | Status** |
|---|---|---|---|---|---|---|---|---|---|
| 101004 CH: 4.0 mg VS: 200 mg | Colorectal | NRAS, MSI stable | 22 Mar. 2018 | SD | +11 (Cycle 2) | SD | −54 (Cycle 2) | N/A | Off study after Cycle 4 |
| 101013 CH: 4.0 mg VS: 200 mg | Rectal cancer | NRAS, ATM loss | 19 Sep. 2018 | SD | +11 (Cycle 2) | SD | −50 (Cycle 4) | −29 (Cycle 4) | Off study after Cycle 4 |

**Data cut off 18 Jun. 2019

TABLE 4

Combination of CH5126766 and VS-6063 administered to patients with pancreatic cancer

| Trial ID Dose level | Tumor types | mutation | First dose | Best Response | % tumor size | Overall Response | CA19-9 level % | Status** |
|---|---|---|---|---|---|---|---|---|
| 102003 CH: 4.0 mg VS: 200 mg | Pancreatic adenocarcinoma | KRAS | 16 Nov. 2018 | SD | −19 (Cycle 2) | SD | −54 (Cycle 4) | Off study after Cycle 6 |

**Data cut off 18 Jun. 2019

The invention claimed is:

1. A method of treating ovarian cancer or non-small cell lung cancer in a subject in need thereof, the method comprising orally administering to the subject an effective amount of CH5126766, or a pharmaceutically acceptable salt thereof, in combination with an effective amount of defactinib, or a pharmaceutically acceptable salt thereof, wherein CH5126766, or a pharmaceutically acceptable salt thereof, and defactinib, or a pharmaceutically acceptable salt thereof, are administered as a cycle comprising administering CH5126766, or a pharmaceutically acceptable salt thereof, twice a week and defactinib, or a pharmaceutically acceptable salt thereof, twice daily for three weeks and then not administering CH5126766, or a pharmaceutically acceptable salt thereof, and defactinib, or a pharmaceutically acceptable salt thereof, for one week.

2. The method of claim 1, wherein CH5126766, or a pharmaceutically acceptable salt thereof, is administered at a dose of 0.5 mg to 10 mg per administration.

3. The method of claim 2, wherein CH5126766, or a pharmaceutically acceptable salt thereof, is administered at a dose of 3.2 mg per administration.

4. The method of claim 2, wherein CH5126766, or a pharmaceutically acceptable salt thereof, is administered at a dose of 4 mg per administration.

5. The method of claim 1, wherein defactinib, or a pharmaceutically acceptable salt thereof, is administered at a dose of 100 mg to 500 mg per administration.

6. The method of claim 5, wherein defactinib, or a pharmaceutically acceptable salt thereof, is administered at a dose of 200 mg per administration.

7. The method of claim 5, wherein defactinib, or a pharmaceutically acceptable salt thereof, is administered at a dose of 400 mg per administration.

8. The method of claim 1, wherein the cancer is characterized as having a mutation in EGFR, FGFR, ALK, ROS1, PI3K, NF-1, BRAF, HRAS, KRAS or NRAS.

9. The method of claim 1, wherein the cancer is characterized as having a mutation in RAS, BRAF, or NF-1.

10. The method of claim 9, wherein the mutation in RAS is a mutation in HRAS, KRAS, or NRAS.

11. The method of claim 1, wherein the ovarian cancer is low grade serous ovarian cancer.

12. The method of claim 1, wherein CH5126766, or a pharmaceutically acceptable salt thereof, is a potassium salt of CH5126766.

* * * * *